United States Patent
Pilgeram et al.

(10) Patent No.: US 10,828,146 B2
(45) Date of Patent: Nov. 10, 2020

(54) INSTRUMENTATION FOR SOFT TISSUE RECONSTRUCTION

(71) Applicant: Stryker Corporation, Kalamazoo, MI (US)

(72) Inventors: Kyle Craig Pilgeram, San Jose, CA (US); Ran Oren, Kibbutz Gaaton (IL); Elad Rash, Beit Lehem Haglilit (IL); Miguel Figueroa, Juana Diaz, PR (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/668,339

(22) Filed: Aug. 3, 2017

(65) Prior Publication Data
US 2018/0036114 A1    Feb. 8, 2018

Related U.S. Application Data

(60) Provisional application No. 62/371,005, filed on Aug. 4, 2016.

(51) Int. Cl.
*A61F 2/08* (2006.01)
*A61B 17/04* (2006.01)
*A61B 90/00* (2016.01)

(52) U.S. Cl.
CPC ........ *A61F 2/0805* (2013.01); *A61B 17/0482* (2013.01); *A61B 90/06* (2016.02);
(Continued)

(58) Field of Classification Search
CPC ...... A61F 2/0805; A61F 2/0811; A61B 90/06; A61B 17/0482
See application file for complete search history.

(56) References Cited

U.S. PATENT DOCUMENTS

| 4,772,286 A | 9/1988 | Goble et al. |
| 5,632,748 A | 5/1997 | Beck, Jr. et al. |

(Continued)

FOREIGN PATENT DOCUMENTS

| JP | 5300917 B2 | 9/2013 |
| WO | 2008002550 A2 | 1/2008 |
| WO | 2012158583 A1 | 11/2012 |

OTHER PUBLICATIONS

Extended European Search Report for Application No. EP17184802.1 dated Dec. 8, 2017.

*Primary Examiner* — Christopher D. Prone
*Assistant Examiner* — Christine L Nelson
(74) *Attorney, Agent, or Firm* — Lerner, David, Littenberg, Krumholz & Mentlink, LLP

(57) ABSTRACT

The present disclosure includes, in one embodiment, a tensioner instrument having a body having a channel and a plurality of arms projecting outward from the body, each arm including a cleat having a slot adapted to receive a suture; a base member positioned within the channel of the body; an actuating mechanism having a first coupling member adapted to engage a second coupling member on the body to removeably couple the actuating mechanism to the body; and a universal joint adapted to allow for relative movement between the base member and the body such that, when each suture is positioned within each cleat and the actuating mechanism is actuated, the tensioner applies uniform tension to each suture positioned in each cleat.

19 Claims, 26 Drawing Sheets

(52) U.S. Cl.
CPC ..... *A61F 2/0811* (2013.01); *A61B 2017/0496* (2013.01); *A61B 2090/064* (2016.02); *A61F 2002/0823* (2013.01); *A61F 2002/0829* (2013.01); *A61F 2002/0835* (2013.01); *A61F 2002/0858* (2013.01); *A61F 2002/0864* (2013.01); *A61F 2002/0882* (2013.01); *A61F 2220/0075* (2013.01); *A61F 2220/0091* (2013.01); *A61F 2230/0069* (2013.01); *A61F 2250/0018* (2013.01); *A61F 2250/0029* (2013.01)

(56) References Cited

U.S. PATENT DOCUMENTS

| | | | |
|---|---|---|---|
| 5,702,447 | A | 12/1997 | Ivalch et al. |
| 5,713,897 | A | 2/1998 | Goble et al. |
| 5,720,753 | A | 2/1998 | Sander et al. |
| 5,725,529 | A | 3/1998 | Nicholson et al. |
| 5,899,938 | A | 5/1999 | Sklar et al. |
| 5,906,632 | A | 5/1999 | Bolton |
| 6,221,107 | B1 | 4/2001 | Steiner et al. |
| 6,533,816 | B2 | 3/2003 | Sklar |
| 6,547,778 | B1 | 4/2003 | Sklar et al. |
| 6,554,862 | B2 | 4/2003 | Hays et al. |
| 6,562,043 | B1 | 5/2003 | Chan |
| 6,562,071 | B2 | 5/2003 | Jarvinen |
| 6,679,889 | B1 | 1/2004 | West, Jr. et al. |
| 6,755,840 | B2 | 6/2004 | Boucher et al. |
| 6,887,271 | B2 | 5/2005 | Justin et al. |
| 7,211,111 | B2 | 5/2007 | Boucher et al. |
| 7,235,100 | B2 | 6/2007 | Martinek |
| 7,309,355 | B2 | 12/2007 | Donnelly et al. |
| 7,731,750 | B2 | 6/2010 | Bojarski et al. |
| 7,850,711 | B1 | 12/2010 | Stone et al. |
| 7,967,861 | B2 | 6/2011 | Montgomery et al. |
| 7,988,732 | B2 | 8/2011 | Bojarski et al. |
| 8,016,865 | B2 | 9/2011 | Donnelly et al. |
| 8,048,158 | B2 | 11/2011 | Hays et al. |
| 8,057,524 | B2 | 11/2011 | Meridew |
| 8,100,968 | B2 | 1/2012 | Chan |
| 8,105,343 | B2 | 1/2012 | White et al. |
| 8,162,978 | B2 | 4/2012 | Lombardo et al. |
| 8,197,485 | B2 * | 6/2012 | Marshall ............... A61F 2/0805 606/144 |
| 8,221,498 | B2 | 7/2012 | Boucher et al. |
| 8,226,714 | B2 | 7/2012 | Beck, Jr. et al. |
| 8,414,647 | B2 | 4/2013 | Baird et al. |
| 8,435,293 | B2 | 5/2013 | Donnelly et al. |
| 8,465,545 | B2 | 6/2013 | Montgomery et al. |
| 8,491,632 | B2 | 7/2013 | Stone et al. |
| 8,491,652 | B2 | 7/2013 | Fening et al. |
| 8,523,902 | B2 | 9/2013 | Heaven et al. |
| 8,562,680 | B2 | 10/2013 | Hays et al. |
| 8,647,385 | B2 | 2/2014 | Boucher et al. |
| 8,657,880 | B2 | 2/2014 | Paulos |
| 8,663,325 | B2 | 3/2014 | Graf et al. |
| 8,696,720 | B2 | 4/2014 | Lazarof |
| 8,734,497 | B2 | 5/2014 | Goel et al. |
| 8,740,939 | B2 | 6/2014 | Stone et al. |
| 8,747,469 | B2 | 6/2014 | Wang et al. |
| 8,771,352 | B2 | 7/2014 | Conner et al. |
| 8,778,023 | B2 | 7/2014 | Sklar |
| 8,956,410 | B2 | 2/2015 | Donnelly et al. |
| 8,968,402 | B2 | 3/2015 | Myers et al. |
| 9,089,416 | B2 | 7/2015 | Ammann |
| 9,216,078 | B2 | 12/2015 | Conner et al. |
| 9,265,602 | B2 | 2/2016 | Beck, Jr. et al. |
| 2003/0130735 | A1 | 7/2003 | Rogalski |
| 2006/0149258 | A1 | 7/2006 | Sousa |
| 2007/0038221 | A1 | 2/2007 | Fine et al. |
| 2011/0071579 | A1 | 3/2011 | Reach, Jr. |
| 2011/0184438 | A1 | 7/2011 | Hoof |
| 2012/0109299 | A1 | 5/2012 | Li et al. |
| 2012/0203339 | A1 | 8/2012 | Heaven |
| 2013/0184720 | A1 | 7/2013 | Aldridge et al. |
| 2013/0304120 | A1 | 11/2013 | Stone et al. |
| 2014/0094860 | A1 | 4/2014 | Reimels |
| 2015/0012094 | A1 | 1/2015 | Denham et al. |
| 2015/0142110 | A1 | 5/2015 | Myers et al. |
| 2015/0173887 | A1 | 6/2015 | Berelsman et al. |
| 2015/0320545 | A1 | 11/2015 | Boucher et al. |
| 2016/0022414 | A1 | 1/2016 | Ammann |

* cited by examiner

INSTRUMENTATION FOR SOFT TISSUE RECONSTRUCTION

CROSS-REFERENCE TO RELATED APPLICATIONS

The present application claims the benefit of the filing date of U.S. Provisional Patent Application No. 62/371,005 filed Aug. 4, 2016, the disclosure of which is hereby incorporated herein by reference.

BACKGROUND OF THE INVENTION

The present disclosure relates generally to implants, instrumentation, kits and methods for repairing damage to soft tissue, including soft tissue such as tendons and ligaments, and particularly the anterior cruciate ligament (ACL) in the knee joint. The ACL is exposed to significant forces simply by use of the knee in everyday activities, but the ACL can also experience even greater forces, and as such ACL injuries are often caused by a sudden force applied to the knee, and are a common form of injury in athletic activities. The injury occurs typically when the knee is bent or twisted in an awkward direction.

Current implants, instrumentation, kits and methodologies for tensioning and securing soft tissue to bone can be challenging to use successfully, particularly when used to replace and/or repair a soft tissue that is exposed to greater forces than normal, such as the anterior cruciate ligament (ACL). For example, issues tend to arise when an operator (e.g., a surgeon or the like) attempts to obtain a desired tension on the soft tissue, particularly where the soft tissue has a multi-strand construction, such that each end of the replacement graft includes multiple attachment points. This is particularly difficult in a reconstruction of a torn ACL in a knee of a patient. In such a reconstruction, the operator must properly tension the replacement ACL graft, which is typically formed in a multi-strand construction, and securely fix the graft in the bone tunnel, to ensure a successful result. This tensioning step can be particularly troublesome since the operator should tension each strand evenly, such that each strand can equally accommodate a load applied to the graft, which can be a difficult and time-consuming task.

Similarly, the securing step has its own challenges in that traditional interference screws can damage the graft, while other types of implants can loosen and result in an unsatisfactory repair. For instance, oftentimes a sheath is positioned between the interference screw and soft tissue and/or suture. The sheath provides separation between the soft tissue and the fixation member, which may help to prevent damage to the soft tissue. Additionally, the sheath may help to prevent the soft tissue and/or suture from wrapping around the threads of the screw as the screw is rotated into position. In this manner, the sheath may limit movement, including rotation and migration, of the soft tissue and screw relative to the bone hole. However, such sheaths can also result in insufficient fixation of the soft tissue and/or suture due to the separation of the soft tissue and/or suture from the interference screw. Still further, such sheaths can even cause pinch points or unequal fixation of the soft tissue and/or suture along its length, thus exposing the soft tissue and/or suture to damage.

These steps are often times difficult to perform successfully, and thus, have a tendency to reduce the effectiveness of such repairs. Thus, there is a need in the art for improved implants, instrumentation, kits and methods for repairing and/or replacing soft tissue such that these procedures can be performed efficiently, effectively and successfully.

BRIEF SUMMARY OF THE INVENTION

The present disclosure relates generally to various implants, instruments, kits, and methods for use in securing soft tissue, suture, or both in combination, to bone. More particularly, the present disclosure relates to soft tissue implants and instrumentation for implantation of such implants. The implants, instruments, kits, and methods may be used in the reconstruction, repair or replacement (generally referred to herein as reconstruction) of soft tissue in a human or other animal. For example, the implant and accompanying instrumentation may be used in the reconstruction of an anterior cruciate ligament (ACL) in the knee joint of a human patient. In this manner, the implant, along with the soft tissue and/or suture, may be inserted into a bone tunnel in a femur or tibia formed during ACL replacement surgery to secure the soft tissue and/or suture therein. While this example of an ACL replacement and/or fixation will be used throughout this disclosure, the implants, instruments, and methods can be used in other anatomical locations and on other soft tissue in an animal.

A first aspect of the present disclosure is a sheath for use in securing a filamentary member to bone including a first sheath body extending a length from a distal end to a proximal end and including a plurality of first ribs extending transversely to the length and a plurality of second ribs extending transversely to the length, the plurality of first ribs positioned along a first lateral edge of the first sheath body and the plurality of second ribs positioned along a second lateral edge of the first sheath body, and a second sheath body extending along a length from a distal end to a proximal end and including a plurality of first ribs extending transversely to the length and a plurality of second ribs extending transversely to the length, the plurality of first ribs positioned along a first lateral edge of the second sheath body and the plurality of second ribs positioned along a second lateral edge of the second sheath body, with the first and second sheath bodies positioned relative one another where the first edge of the first sheath body is adjacent the first edge of the second sheath body, and where the second edge of the first sheath body is adjacent the second edge of the second sheath body, the plurality of first ribs of the first sheath body interdigitate with the plurality of first ribs of the second sheath body and the plurality of second ribs of the first sheath body interdigitate with the plurality of second ribs of the second sheath body.

In other embodiments, at least one rib of at least one of the pluralities of ribs may include a tab on an end of the rib. At least one rib of the plurality of ribs opposite the at least one rib including the tab may include a stop, the stop adapted to engage the tab as the first sheath body and second sheath body move away from one another in a direction transverse to the length. The proximal end of the first and second sheath bodies may flare outwards such that the proximal end of the sheath has a larger diameter than a diameter of the first and second sheath bodies in between the proximal and distal ends. The first edges of the first and second sheath bodies and the second edges of the first and second sheath bodies may be offset on a circumference of the sheath. The distal end of the first and second sheath bodies may taper inwardly such that the distal end of the sheath has a smaller diameter than a diameter of the first and second sheath bodies in between the proximal and distal ends. The first and second sheath bodies may each be generally convex such that the sheath bodies together form a generally cylindrical shaped sheath. The sheath may be adapted to accept a fixation device between the proximal ends of the first and second sheath bodies.

A second aspect of the present disclosure is an expandable sheath including a cannulated body defining a longitudinal axis and including an outer tubular member including an outer wall and an inner surface, the outer wall defining a channel extending between a proximal end and a distal end, and an inner member including an inner surface and being positioned at least partially within the outer tubular member, at least one of the inner surfaces of the members including a plurality of teeth projecting from the inner surface adapted to engage a fixation member.

In other embodiments, the sheath may include a tapered distal tip. The cannulated body may flare outward near a proximal end of the body. The outer tubular member and the inner member may both include a plurality of teeth projecting from the respective inner surface. The sheath may include a flange projecting from the outer wall of the outer tubular member, the flange adapted to provide a stop surface upon insertion of the sheath into bone. The outer wall of the outer tubular member may include biased barbs adapted to engage a graft. An outer radius of the inner member may be greater than an inner radius of the outer tubular member. A portion of the inner member may extend further proximally than the outer tubular member.

Another aspect of the present disclosure is an expandable sheath including a cannulated body including a first member including a first plurality of interdigitating ribs, and a second member including a second plurality of interdigitating ribs for mating engagement with the first plurality of interdigitating ribs, interaction of the first and second pluralities of ribs maintains the positioning of the first and second members relative to one another.

In other embodiments, in an initial position, the ribs may form a substantially continuous surface. The interdigitating ribs may extend along more than half of a length of the cannulated body. The cannulated body may have a horizontal axis and a vertical axis, both axes being transverse to a longitudinal axis extending along a length of the cannulated body, the horizontal and vertical axes defining four quadrants of the cannulated body, the interdigitating ribs defining two opposing quadrants. At least one of the ribs of one of the first or second member may include a tab projecting from the rib and at least one of the opposing and interdigitating ribs of the other of the first or second member including a stop, the tab interacting with the stop to inhibit separation of the first and second members from one another.

Another aspect of the present disclosure is a tensioner including a body having a channel and a plurality of arms projecting outward from the body, each arm including a cleat having a slot adapted to receive a suture, a base member positioned within the channel of the body, an actuating mechanism having a first coupling member adapted to engage a second coupling member on the body to removeably couple the actuating mechanism to the body, and a universal joint adapted to allow for relative movement between the base member and the body such that, when each suture is positioned within each cleat and the actuating mechanism is actuated, the tensioner applies uniform tension to each suture positioned in each cleat.

In other embodiments the universal joint may include a first portion and a second portion of the outer surface of the base member forming convex surfaces and a first portion and second portion of the inner surface of the body forming concave surfaces, wherein the first concave surface receives the first convex surface and the second concave surface receives the second convex surface. Each arm may be pivotable in all directions relative to the body. The first coupling member may be a projection disposed on the actuating mechanism and the second coupling member may be an opening on the body for receiving the projection. The actuating mechanism may be spring actuated. The tensioner may include a tension gauge for indicating the amount of force applied to the spring. The plurality of arms may be four arms. The tensioner may include a foot positioned on the base member. The tensioner may extend along a longitudinal axis, the tensioner being symmetrical on either side of the longitudinal axis. The arms may be positioned near a distal end of the body.

Another aspect of the present disclosure is a tensioner including a body having a channel and a plurality of arms projecting outward from the body, each arm including a cleat having a slot adapted to receive a suture, a base member positioned within the channel of the body, and an actuating mechanism having a first coupling member adapted to engage a second coupling member on the body to removeably couple the actuating mechanism to the body, the tensioner is movable between a rest condition in which the first coupling member of the actuating mechanism is engaged with the corresponding second coupling member of the body, such that the body is stationary relative to the base member, and an actuated condition in which the first coupling member and the second coupling member disengage to allow relative movement between the body and the base member.

In other embodiments, the actuating mechanism may be moveable between an initial position in which the tensioner is in the rest condition and a final position in which the tensioner is in the actuated condition. A portion of an outer surface of the base member may form a convex surface and a portion of an inner surface of the body may form a corresponding concave surface for receiving the convex surface, the corresponding surfaces allowing relative movement of the body with respect to the base member. The convex surface of the base member and the concave surface of the body may form a universal connection. In the actuated position, the plurality of arms may be laterally adjustable relative to the body. When each suture is positioned within each cleat, the tensioner may be adapted to apply uniform tension to each suture. The tensioner may include a universal joint that includes a first portion and a second portion of the outer surface of the base member forming convex surfaces and a first portion and second portion of the inner surface of the body forming concave surfaces, the first concave surface receives the first convex surface to form a first ball-and-socket arrangement and the second concave surface receives the second convex surface to form a second ball-and-socket arrangement.

Another aspect of the present disclosure includes a system for securing and tensioning graft including a sheath, a sheath inserter, and a tensioner including a body having a channel, through which the sheath inserter is positioned, and a plurality of arms projecting outward from the body, each arm including a cleat having a slot adapted to receive a suture and/or a portion of the graft, with the suture positioned in the slots of the cleats, the tensioner simultaneously tensions the suture.

In other embodiments, the sheath may be expandable such that, with the sheath in position and the tensioner tensioning the suture, the sheath is adapted to be expanded to secure the suture and/or a portion of the graft. The plurality of arms may be laterally adjustable relative to the body such that the tensioner is adapted to apply uniform tension to each suture positioned in each cleat. The plurality of arms and body of the tensioner may be connected by a universal joint such that the tensioner is adapted to apply uniform tension to each suture positioned in each cleat.

Another aspect of the present disclosure is a method of securing and tensioning graft including inserting a sheath and at least two graft strands inside a bone tunnel, securing a first graft strand a first cleat of an arm of a tensioner and securing a second graft strand on a second cleat of a second arm of the tensioner, tensioning each of the first and second graft strands simultaneously and with substantially equal tension, and expanding the sheath with a fixation member, which secures the graft strands relative to the bone tunnel.

Another aspect of the present disclosure is a method of securing and tensioning graft including securing a first graft strand on a first cleat of an arm of a tensioner with a first tension and securing a second graft strand on a second cleat of a second arm of the tensioner with a second tension, the first and second tension being different, and tensioning each of the first and second grafts to a third tension, the third tension being different from the first and second tensions, the tensioning of the first and second grafts to the third tension occurring simultaneously.

In other embodiments, during the tensioning step, the arms of the tensioner may pivot in all directions relative to a body of the tensioner. The tensioner may include a base, the base forming a universal joint with the arms, such that the arms move in any direction relative to the base. The movement of the arms may cause the simultaneous tensioning of each of the graft strands.

In another embodiment, the present disclosure includes a method of reconstructing soft tissue, such as repairing damage to soft tissue, including for example tensioning a replacement ACL graft. Such a method may include using a tensioner as defined in any one of the preceding aspects of the disclosure. The method of soft tissue reconstruction may be, for example, reconstruction of a torn ACL in a knee of a patient.

In a further embodiment, the present disclosure includes a method of securing and tensioning soft tissue, such as a graft. Such a method may include, for example, using a system for securing and tensioning a graft as defined in any one of the preceding aspects of the disclosure.

DETAILED DESCRIPTION

Generally, the present disclosure includes devices, assemblies, systems, kits and methods of manufacture, assembly and use for the reconstruction, repair, reattachment, replacement, or otherwise securement of soft tissue. While the following may be used to repair any suitable type of soft tissue—such as meniscus, cartilage, capsule, ligaments and tendons, replacement grafts of any of these soft tissues, or the like, in a knee, hip, ankle, foot, shoulder, elbow, wrist, hand, spine, or any other area of anatomy—reconstructions of an ACL in a knee joint will serve as the primary example of the disclosure below. And more particularly, the primary example of an ACL reconstruction will include the formation of a tibial bone tunnel and a femoral bone tunnel, each of which houses and/or engages one end of an ACL replacement graft. The bone tunnels are intended to be positioned substantially at the location of the native ACL connection sites, though other locations may be used as desired or required based on the specific circumstances of a particular patient or the specific desires of a particular operator.

As used herein unless stated otherwise, the term "anterior" means toward the front part of the body or the face, the term "posterior" means toward the back of the body. The term "medial" means closer to or toward the midline of the body, and the term "lateral" means further from or away from the midline of the body.

Also, when referring to specific directions in the following discussion of a certain device, the terms "proximal" and "distal" are to be understood in regard to the device's orientation and position during exemplary application to human body. Thus, as used herein, the term "proximal" means closer to the operator or in a direction toward the operator, and the term "distal" means more distant from the operator or in a direction away from the operator.

In addition, the terms "about," "generally" and "substantially" are intended to mean that slight deviations from absolute are included within the scope of the term so modified.

As described below, the various implants of the present disclosure, referred to herein as implants, implant sheaths, or sheaths, can be used in conjunction with soft tissue, such as a soft tissue graft, and/or suture. Although only one term may be used in a description for any of these elements, it is to be understood that each can be used alone or in any combination. Further, any fixation member, such as interference screws, plugs, expander bodies, or the like, may be used with any of the following sheath implants, though interference screws are generally exemplified.

Figure 1A:
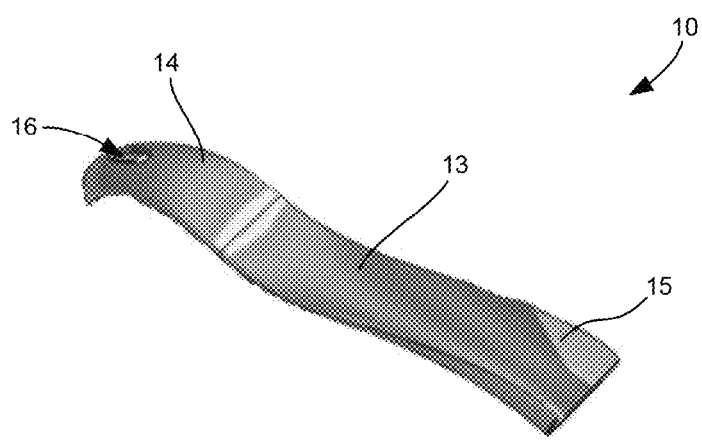
FIGS. 1A-B are top and side perspective views, respectively, of an implant according to an embodiment of the present disclosure.
Figure 1B:
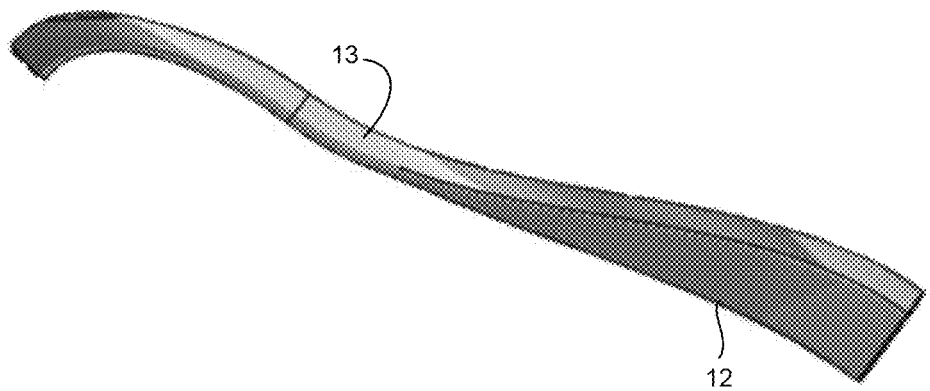
Figure 1C:
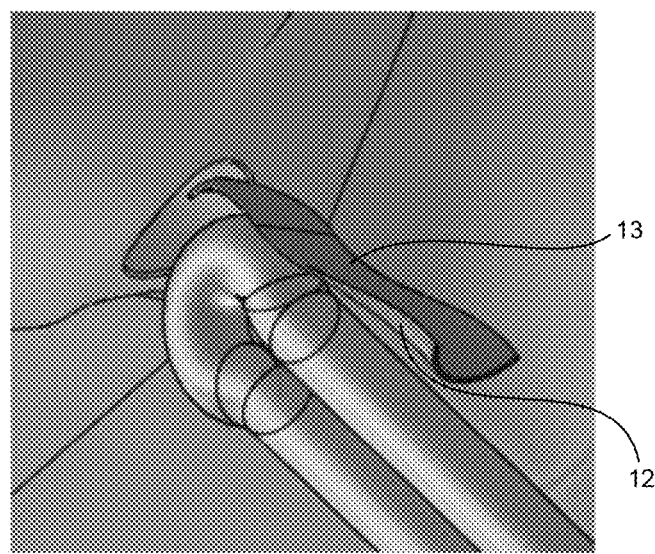
FIG. 1C is a schematic representation of the implant of FIGS. 1A-B in conjunction with soft tissue or graft during insertion of the same in a bone tunnel.

In one embodiment of the present disclosure, FIGS. 1A-C show implant 10 and an exemplary use in a bone tunnel during ACL replacement surgery. Implant 10 is a sheath implant having lower and upper surfaces 12, 13 extending between a distal end 14 and a proximal end 15. Upper surface 13 is generally concave near proximal end 15, and lower surface 12 is generally concave near distal end 14. As a result, sheath 10 has a wave-like shape. Sheath 10 may include an eyelet hole, such as the eyelet hole 16 as illustrated extending through upper surface 13 and lower surface 12 near distal end 14 for receiving a leading suture, graft support, suture secured to a button anchor, or the like, as known in the art. Although shown as an eyelet, sheath 10 can include any attachment feature positioned on the sheath, and particularly on the distal end 14, for attaching suture. Further, an alternative attachment feature near the location of eyelet 16 could be used to push implant 10 into position, such as a threaded or press fit hole for use with a mating insertion rod. Sheath 10 may be a monolithic, one-piece construct, which allows for simplified manufacturing. The sheath 10 may also include a tapered surface, which may be near distal end 14, such that the width of the distal end may be less than the width of the proximal end, for example.

As shown in FIG. 1C, soft tissue may be positioned along the concave portion of lower surface 12 and extend proximally along the length of sheath 10. A fixation member, such as an interference screw (not shown), may be positioned above the concave portion of upper surface 13. During use, as the fixation member or screw is moved into position, sheath 10 is pushed against the soft tissue and the bone tunnel. In this manner, with the sheath 10, soft tissue and fixation member positioned within a bone tunnel, the sheath would separate the soft tissue from the fixation member. This can provide additional fixation of the soft tissue (which may be in addition to a suture button, as known in the art) to the bone while minimizing the risk of the fixation member damaging the soft tissue. Additionally, the wave-like shape of sheath 10 may impart additional fixation of the soft tissue along more, if not all, of the length of sheath 10. Similarly, the shape of upper surface 13 of the wave-like shape may promote better fixation between sheath 10 and the fixation member.

Figure 2:
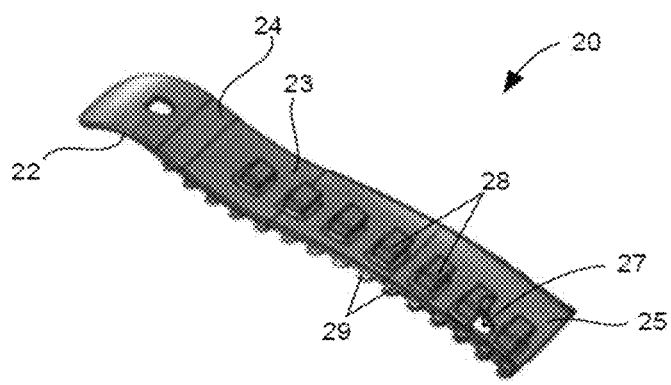
FIG. 2 is a top perspective view of an implant according to another embodiment of the present disclosure.

In another embodiment, FIG. 2 shows implant 20 that is identical to implant 10 in most respects. Similar components are not described again, but include upper surface 23, lower surface 22, distal end 24, and proximal end 25. Sheath implant 20 includes an additional eyelet hole 27 positioned near proximal end 25 of the sheath. Proximal hole 27 may allow for engagement of a trailing suture to help provide control of the sheath 20 during insertion. For example, proximal hole 27 allows sheath 20 to be pulled proximally if the position of the sheath needs to be adjusted. Sheath 20 also includes a screw engagement feature for engaging the screw. In the illustrated embodiment, the engagement feature can be a plurality of teeth 28 projecting outward from upper surface 23 and spaced apart from one another along a portion of the length of the sheath. Teeth 28 allow for guided threading of the screw into the sheath and allow for better securement of the screw to the sheath. Lower surface 22 may also include a securing mechanism for securing soft tissue.

In the illustrated embodiment, the securing mechanism can be a plurality of barbs 29 extending along a portion of the length of the sheath. Each barb 29 extends in a direction generally transverse to the length of sheath 20. The barbs 29 may be biased, so that as the soft tissue is loaded distally, it is gripped by the biased barbs to help prevent the soft tissue from moving in the opposite direction. Although the illustrated embodiment includes generally rectangular teeth 28 and elongated barbs 29, the teeth and barbs may be in any shape, number, and size.

In other examples, a channel (not shown) may extend along the length of sheath 20 on upper surface 23, such that there are two rows of teeth 28. The channel may extend substantially along the midline of the length of the sheath and may provide for passage of a guidewire, if used.

Sheaths 10 and 20 may be used for positioning and securing soft tissue or graft in bone. With respect to ACL surgery, the sheath may be positioned to secure soft tissue in tibial tunnel or the femoral tunnel. With respect to placement in the femoral tunnel, the sheath may be passed through the tibial tunnel and into the femoral tunnel. Alternatively, the sheath may be implanted through an anterior-medial portal via the intraarticular space.

In one embodiment, to use sheath 10 or 20 with soft tissue, the soft tissue is loaded on the generally convex lower surface distally. A guidewire may be positioned on the generally concave upper surface to assist in positioning the sheath, and the sheath and soft tissue are inserted into the bone tunnel. A lead suture in the distal eyelet may be fed up through the femoral tunnel and pulled to assist in moving the sheath and soft tissue into position. After the sheath and soft tissue are positioned in the desired location, the guidewire may remain in the bone tunnel to assist in positioning the screw. The screw is then positioned on the generally concave upper surface. The guide wire is then removed.

Figure 3A:
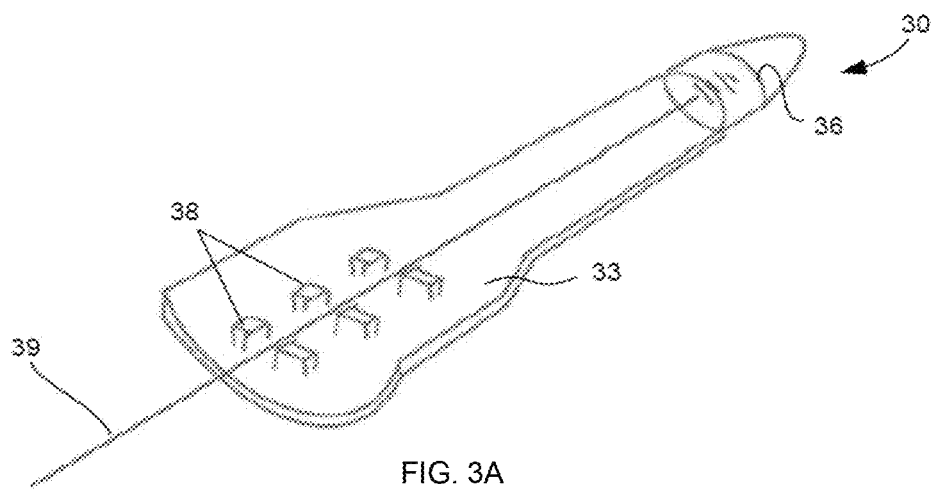
FIG. 3A is a top perspective view of an implant according to yet another embodiment of the present disclosure.

In another embodiment, FIG. 3A shows sheath implant 30 that includes a generally concave upper surface 33 which can have a plurality of teeth 38, similar to teeth 28 of sheath 20. As shown, teeth 38 are separated by a channel that extends along the longitudinal axis of sheath 30. Sheath 30 includes distal nose cone 36, which can include a flat conical portion and ending in a distal tip. The flattened nose provides a low profile of the distal end of sheath 30, which facilitates easier insertion. Guidewire 39 can be positioned within nose cone 36 to allow a user to push sheath 30 into the bone tunnel or to be fed through a cannulated insertion tool.

Figure 3B:
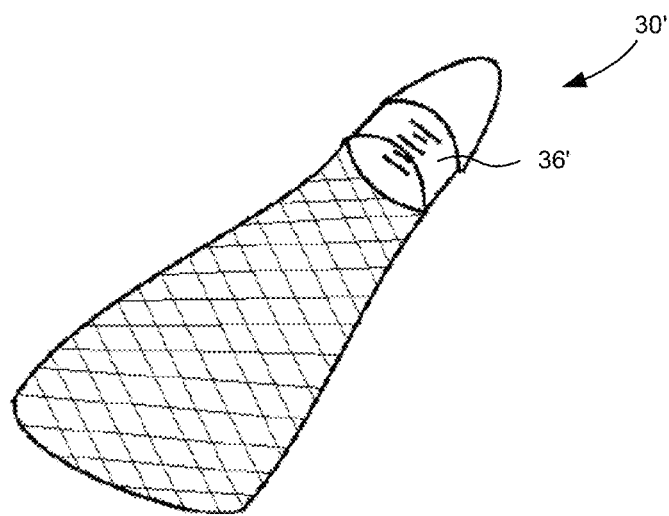
FIG. 3B is a top perspective view of an implant according to yet another embodiment of the present disclosure.
Figure 3C:
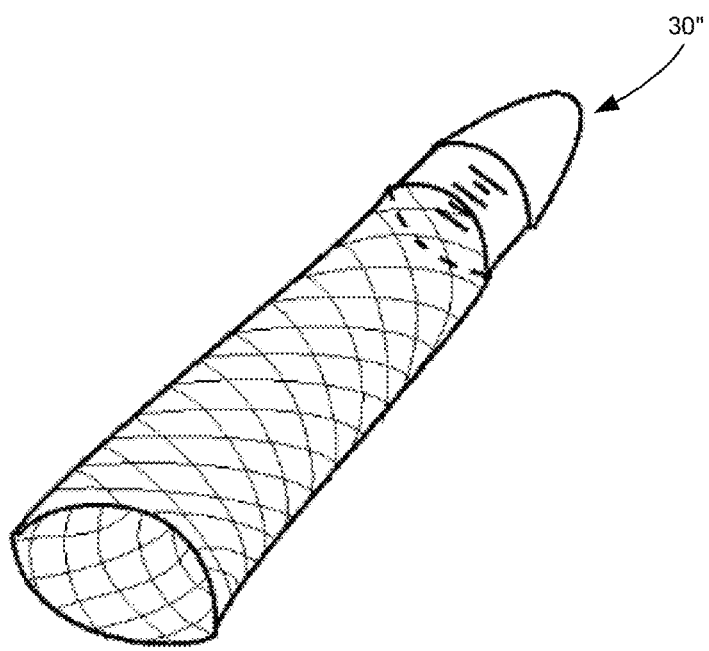
FIG. 3C is a top perspective view of an implant according to yet another embodiment of the present disclosure.

In yet another embodiment, FIG. 3B shows sheath implant 30' which may be a braided, woven or knit filament structure. Sheath 30' may be manufactured from an absorbable material that is coated with a substance to enhance biologic healing. Sheath 30' includes a tip portion including nose cone 36' that may be made of a hard plastic such as polyether ether ketone (PEEK), but other attachment features are possible. In yet another embodiment, FIG. 3C shows sheath implant 30" which may be a braided, woven or knit filament tubular structure to allow a fixation member to be positioned within sheath 30".

Figure 4:
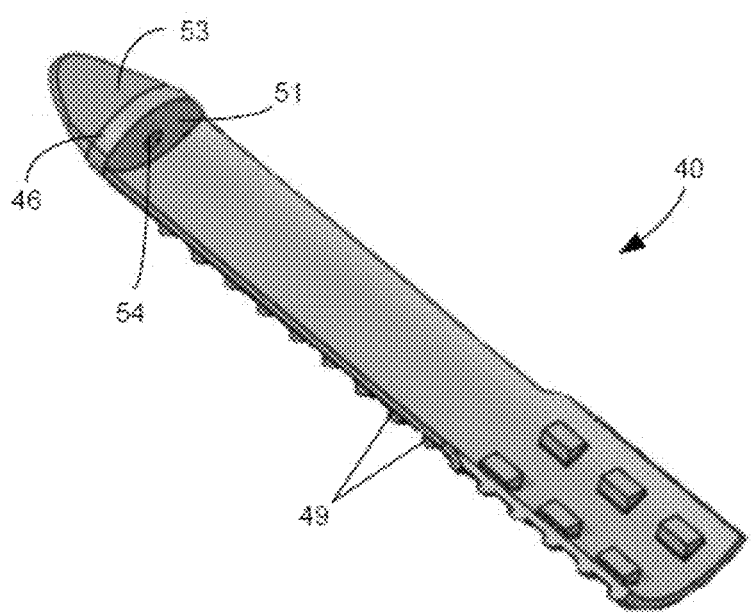
FIG. 4 is a top perspective view of an implant according to still another embodiment of the present disclosure.

In yet another embodiment, FIG. 4 depicts sheath implant 40 that is identical to sheath 30 in most respects, which similar features will not be described again. Sheath 40 includes a connection feature to allow for releaseable attachment of a guide wire with the sheath. The connection feature may be an adhesive, press fit, threaded, or other connection. As illustrated, the connection feature may be bore hole 54. Additionally, sheath 40 includes biased barbs 49 similar to barbs 29 of sheath 20. The bias of barbs 49 may help to prevent soft tissue from slipping when the soft tissue is loaded while still allowing for ease of antegrade insertion of the sheath into the bone tunnel.

In other examples, a passage or breakaway area (not shown) may extend from side surface 51 to top surface 53 of nose cone 46. This may allow for easier removal of the guide wire after the screw is fully seated within the sheath.

Figure 5A:
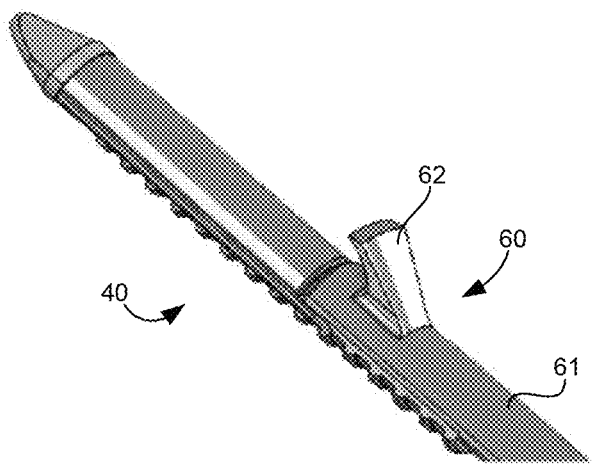
FIGS. 5A-C are schematic perspective views of the implant of FIG. 4 in conjunction with an inserter instrument according to an embodiment of the present disclosure.
Figure 5B:
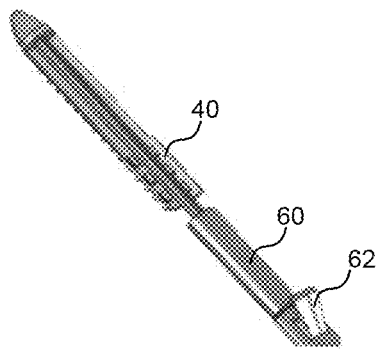
Figure 5C:
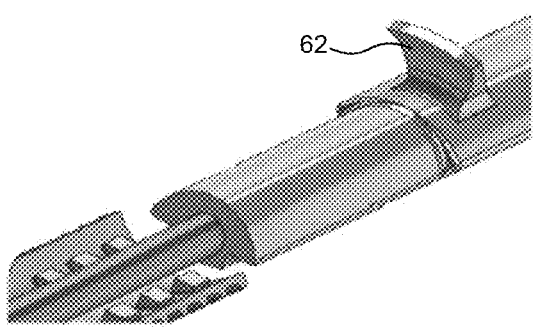

In still another embodiment, FIGS. 5A-C illustrates an example of an implant positioned on an insertion instrument, specifically sheath 40 in combination with inserter instrument 60 for inserting the sheath into a bone tunnel. Inserter 60 may include notcher tip 62 projecting outward from upper surface 61 of the inserter. Upon insertion of inserter 60 into bone, notcher tip 62 provides a notch in the bone surrounding the bone tunnel, which advantageously eliminates an extra step of creating a notch (if desired). The notch helps to ensure that the fixation member, such as the interference screw, stays positioned above sheath 40 in the bone tunnel during insertion of the interference screw into bone since rotation of the screw may coerce the screw to walk around the perimeter of the bone tunnel. In this manner, the notch helps to maintain the configuration of the screw above the sheath and the soft tissue below the sheath and screw.

Figure 6:
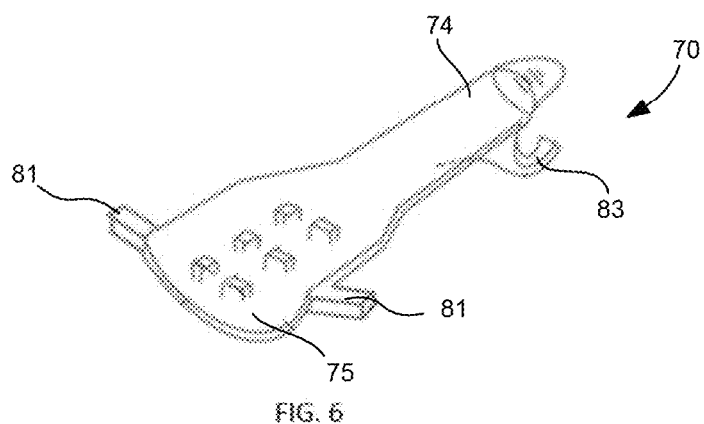
FIG. 6 is a top perspective view of an implant according to a further embodiment of the present disclosure.

In a further embodiment, FIG. 6 illustrates sheath implant 70 including flanges 81 extending outward in a direction generally transverse to the longitudinal axis of the sheath at proximal end 75. Flanges 81 help to prevent over-insertion of sheath 70 as the sheath is inserted into the bone tunnel. Sheath 70 also includes flange 83 near distal end 74 shaped as a "U" or a "C" to engage soft tissue or suture, and in particular the soft tissue or suture that is folded thereon.

Figure 7:
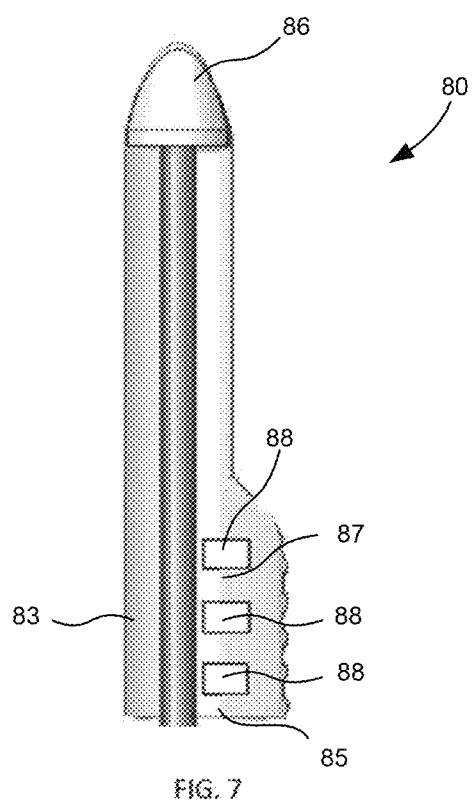
FIG. 7 is a top view of an implant according to yet a further embodiment of the present disclosure.

In another embodiment, FIG. 7 depicts sheath implant 80, which is similar in most respects to sheath 40, except that sheath 80 has an asymmetric shape near its proximal end 85, which is biased to the right side. Sheath 80 includes flange 87 on the right side, which provides protection on the lead side of the screw as the screw is rotated clockwise which could interact with the soft tissue. Sheath 80 includes a plurality of teeth 88 on upper surface 83, similar to the teeth described above. Teeth 88 are not separated by a channel and define one row of teeth extending in a line that is offset from the center of nose cone 86, with the teeth extending on a portion of flange 87. Since the teeth are offset, a guide wire can be received at or near to the center of the nose cone 86. In the illustrated embodiment, there are three teeth 88; however, in alternate embodiments there may be more or less teeth.

Sheaths 30, 40, 70 and 80 may be used in the same manner, as will be described below. In one embodiment, the soft tissue is loaded onto the lower surface of the sheath. A guide wire is placed on the upper surface of the sheath. The sheath and soft tissue are then inserted into the bone tunnel using an inserter similar or identical to inserter 60. The inserter is removed, but the guide wire remains in place on the sheath. A cannulated screw is inserted over the guide wire and rotated to secure the screw to the bone. The guide wire is then pulled or twisted distally to remove the guide wire.

Although the methods described above include inserting the soft tissue and sheath into the bone simultaneously, in an alternative approach, the soft tissue can be positioned within the bone tunnel, such as by using a lead suture or a pushing device, and then the sheath can subsequently be positioned, again by a lead suture, pushing device, or the like.

Any of the sheaths described above may be used in either the femoral or tibial tunnels during soft tissue reconstruction, such as an ACL surgery. However, in a preferred method of use, the above-described sheaths are used in the femoral tunnel to assist in securing the femoral side of the ACL graft, which is typically a long, thin graft which is folded over itself within the femoral tunnel as described above.

Further, the following embodiments of implants can also be used in the repair of soft tissue, for example in reconstruction of an ACL, and as such can be implanted in any bone tunnel, such as for example, the femoral and/or tibial tunnels, and are preferably used in the tibial tunnel. Additionally, each of the sheath implants described below are expandable, such that with a fixation member such as a screw positioned within the implant, the implant expands outwardly.

Figure 8:
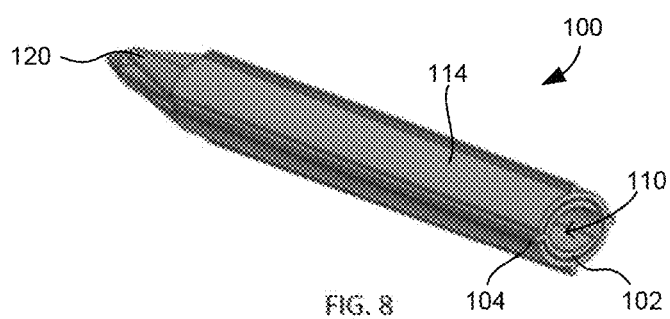
FIG. 8 is a side perspective view of an implant according to still a further embodiment of the present disclosure.

In one embodiment, FIG. 8 depicts sheath implant 100 that includes two sheath bodies, inner body 102 and outer body 114, coupled together with the inner body received within the outer body to form the sheath. Sheath 100 includes passage 110 extending along a longitudinal axis of the sheath for receiving an interference screw. Inner and outer bodies 102, 114 are shaped in the form of a "C," such that each is generally convex, and extends along the longitudinal axis to distal tip 120. Outer body 114 includes a mating feature that corresponds to a mating feature on inner body 102 to secure the two bodies together. In the illustrated embodiment, outer body 114 includes a channel extending along its length, due to the "C" shape of the body, which is adapted to receive flange 104 of inner body. This helps to prevent rotation of the two bodies relative to one another.

Figure 9:
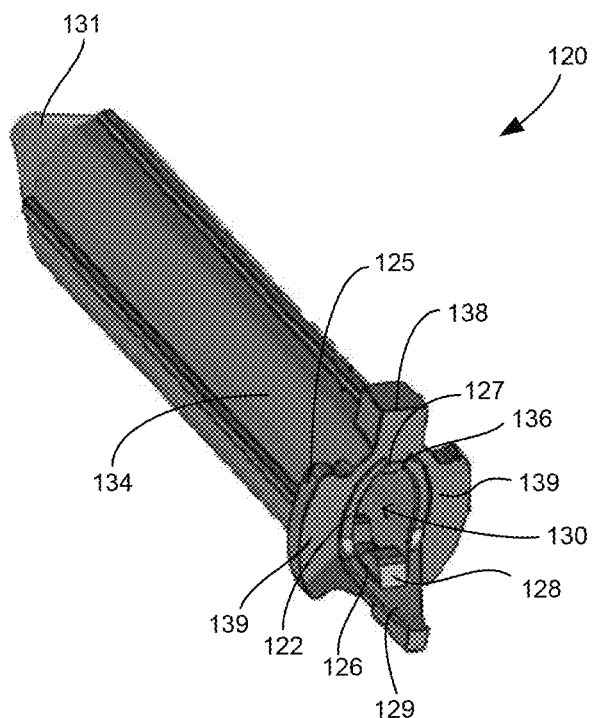
FIG. 9 is a rear perspective view of an implant according to another embodiment of the present disclosure.

In another embodiment, referring to FIG. 9, sheath implant 120 includes two "C" shaped bodies including an inner body 122 attachable with and received within an outer body 134 to form a tubular shaped sheath defining passage 130 for receiving a fixation member. Sheath 120 extends from proximal end 125 to cannulated distal tip 131 along a longitudinal axis. Outer body 134 includes flanges 138, 139 extending outwardly from proximal end 125. Flange 138 extends superiorly from outer body 134 and flanges 139 extend from opposing lateral sides of the outer body. Flanges 138, 139 can be positioned against the cortical surface outside of the tibial tunnel to prevent sheath 120 from advancing too far into the tunnel and beyond the bony, cortical edge of the bone. Additionally, outer body 134 includes a plurality of teeth 127 projecting inferiorly from inner surface 136 toward passage 130 and which can extend a portion of or the entire length of the outer body. Inner body 122 includes teeth 128 projecting upward from inner surface 126 of the inner body toward passage 130. With an interference screw inserted within sheath 120, teeth 127, 128 engage the screw and help to prevent the sheath from migrating relative to the screw when the soft tissue is loaded. Inner body 122 includes lead-in portion 129 that extends further proximally than outer body 134, as a result the length of the inner body is greater than the length of the outer body. Lead-in portion 129 allows for more surface area to allow for easier insertion of the screw into sheath 120 and to guide the screw toward the center of the sheath.

Figure 10A:
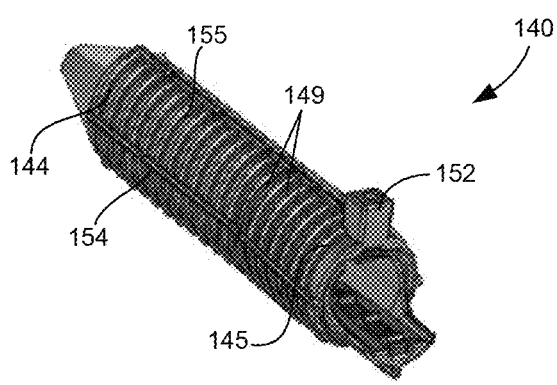
FIGS. 10 A-C are side perspective views of an implant according to yet another embodiment of the present disclosure.
Figure 10B:
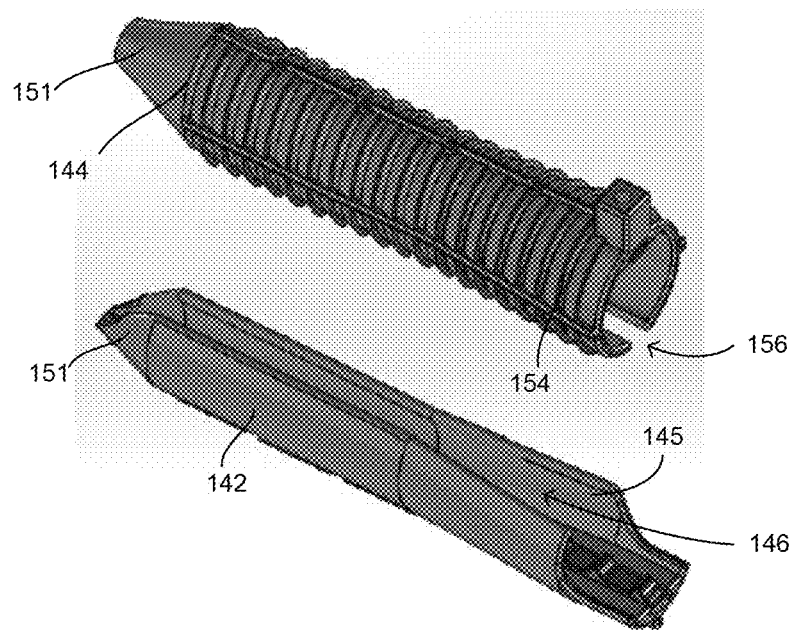
Figure 10C:
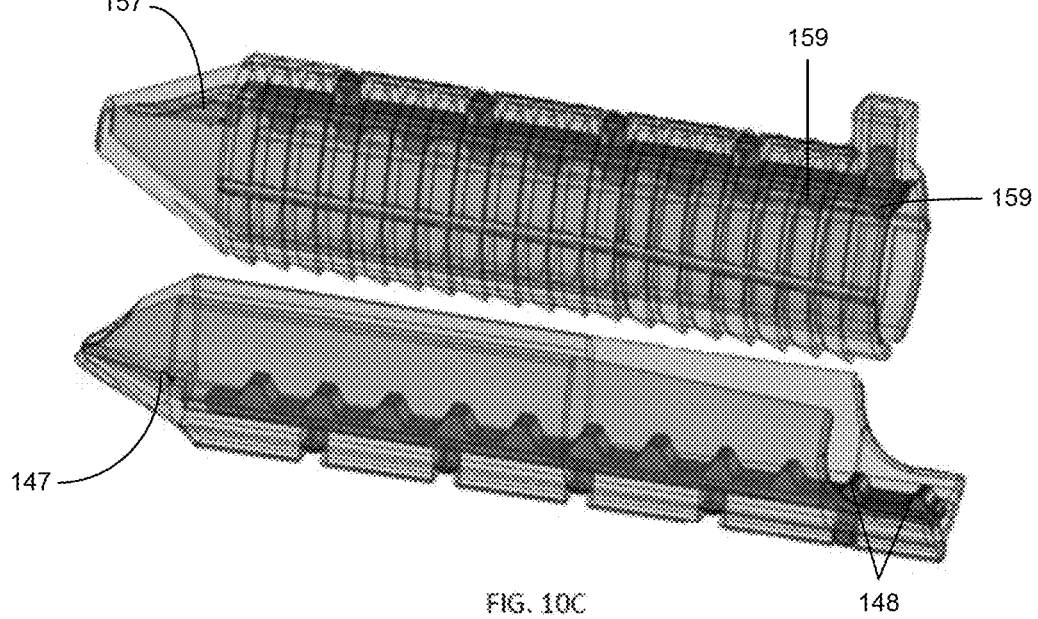

In still another embodiment, FIGS. 10A-C show sheath 140 identical to sheath 120 in many respects, and similar components will not be described again. As best shown in FIGS. 10A-B, sheath 140 includes outer body 154 and inner body 142, each having a generally "C-shape" in that the circumference of each includes an opening that extends the length of the sheath to define channels 156 and 146, respectively. Outer body 154 includes outer surface 155 which has biased barbs 149 positioned around the circumference of the outer surface. Barbs 149 help to grip the soft tissue, when the tissue is loaded physiologically. Furthermore, outer body 154 includes cortical flange 152 positioned near proximal end 145 and extending superiorly from the outer body. Additionally, sheath 140 flares outward at proximal end 145 such that the proximal end has a wider diameter than distal end 144, which provides more space for easier screw starting. Inner body 142 and outer body 154 each taper at distal end 144 to form distal tip 151 of sheath 140. Furthermore, as shown in FIG. 10C, outer body 154 includes expansion member 157 and inner body includes expansion member 147 at distal tip 151. Expansion members 147, 157 allow for greater expansion of distal tip 151, which overcomes the outer distal taper at distal end 144 to facilitate increased compression of the soft tissue against the bone tunnel against a greater length of the sheath, and in particular near the tibial plateau. In the illustrated embodiment, expansion members 147, 157 are in the form of increased material near distal tip 151, such as a flange projecting from the respective inner surface of the body. As best shown in FIG. 10C, outer body 154 includes teeth 159 and inner body includes teeth 148 to engage the screw positioned within passage 146.

Additionally, inner body 142 has an outer radius of curvature that is larger than the inner radius of curvature of outer body 154, which provides an interference fit between the outer body and the inner body. In this manner, the inner and outer bodies 142, 154 experience a fit similar to a radial spring compression fit between them. This prevents inner body 142 from accidentally sliding proximally with respect to outer body 154 and maintains the desired configuration of sheath 140.

In an alternative embodiment, distal end 144 may have an even further reduced diameter to increase the tactile feedback during insertion of the screw. As the screw is twisted during insertion, the torque will increase due to the smaller space available to the screw. Moreover, distal end 144 will have a lower profile for easier insertion of the sheath into the bone tunnel.

In other examples, outer surface 155 of the outer body 154 may be provided with a surface feature such as an increased surface roughness or texture. To achieve this increased roughness, the sheath can be grit blasted, carbide blasted, or the like.

Figure 11A:
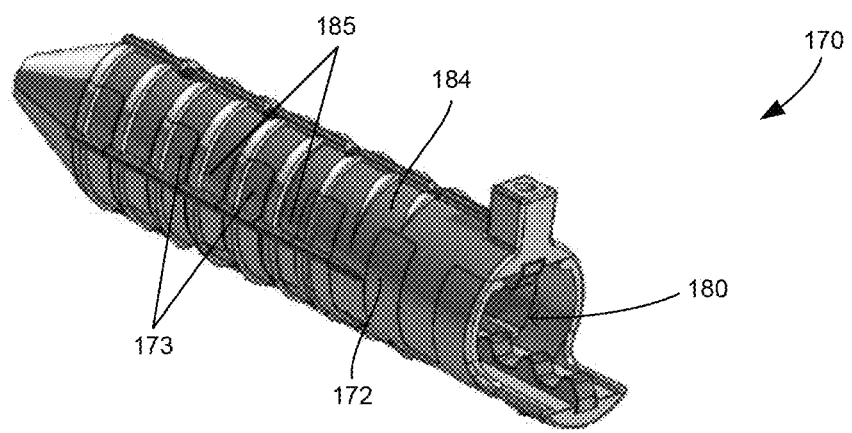
FIGS. 11A-C are side perspective, top perspective, and exploded views, respectively, of an implant according to a further embodiment of the present disclosure.
Figure 11B:
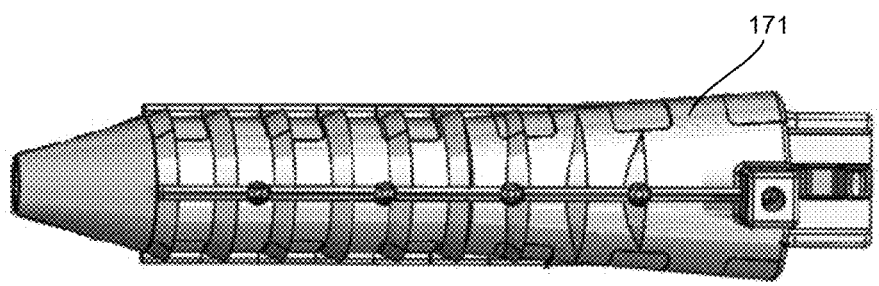
Figure 11C:
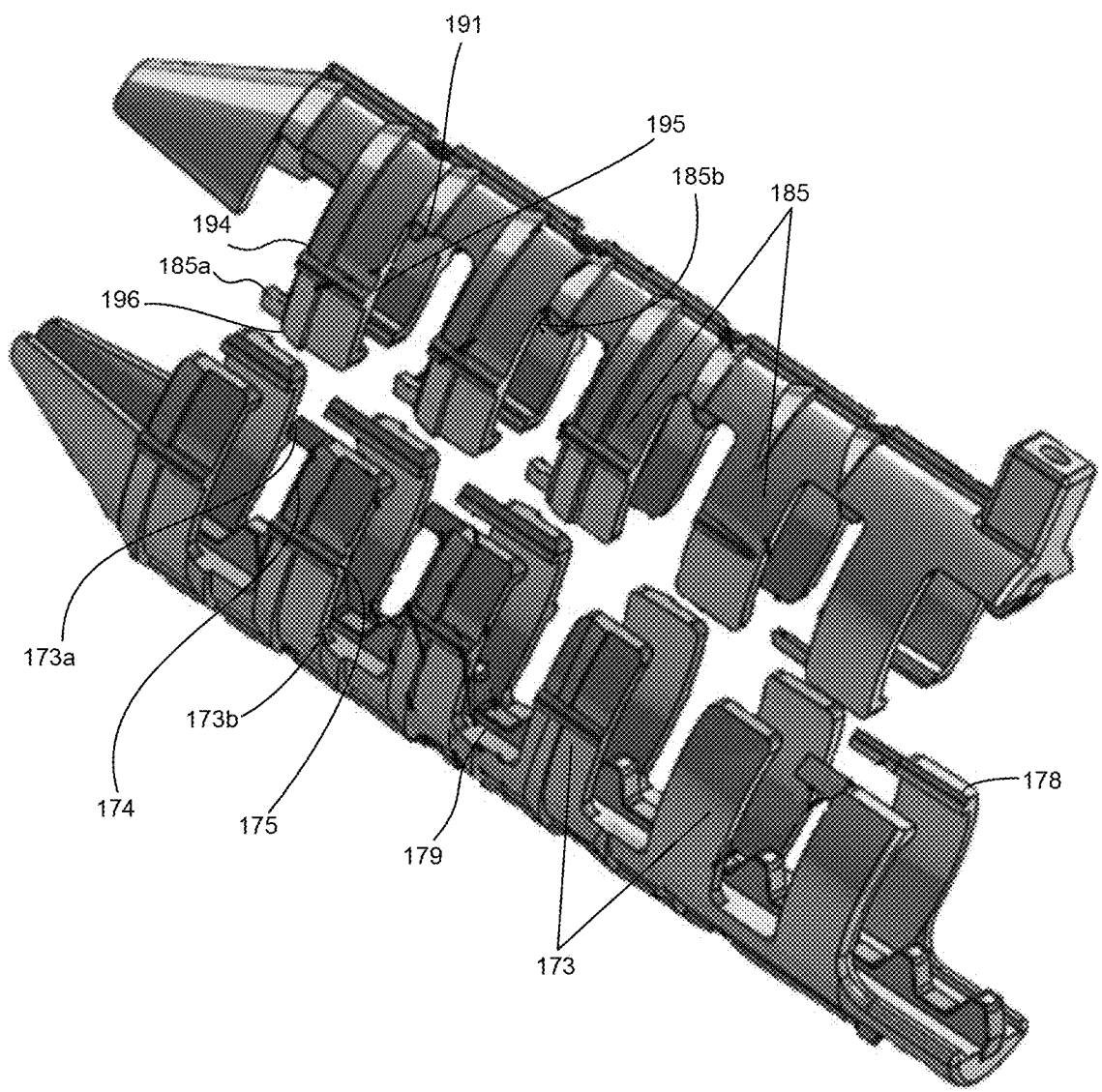
Figure 12A:
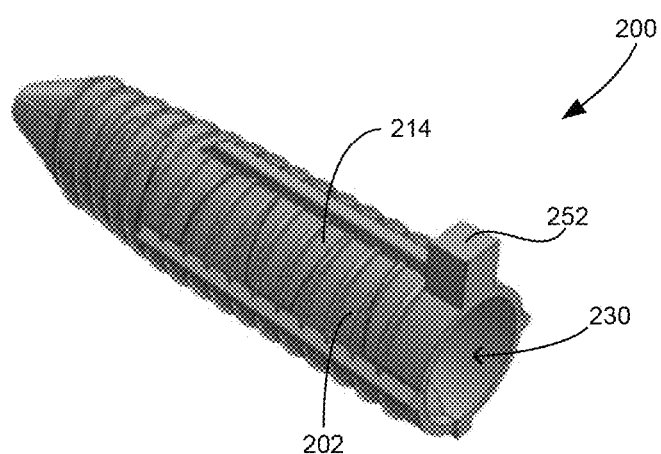
FIGS. 12A-D are perspective sides views and end view of an implant according to another embodiment of the present disclosure.
Figure 12B:
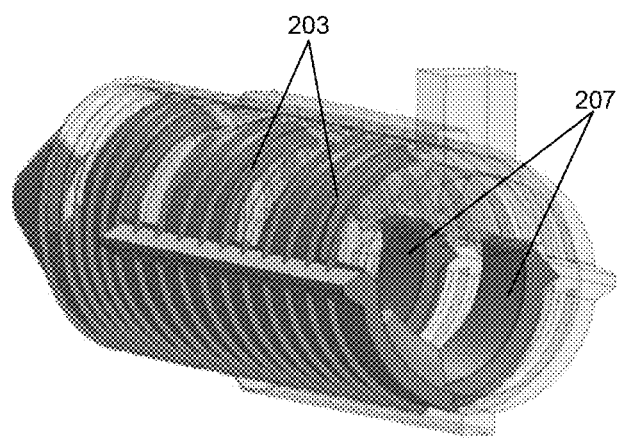
Figure 12C:
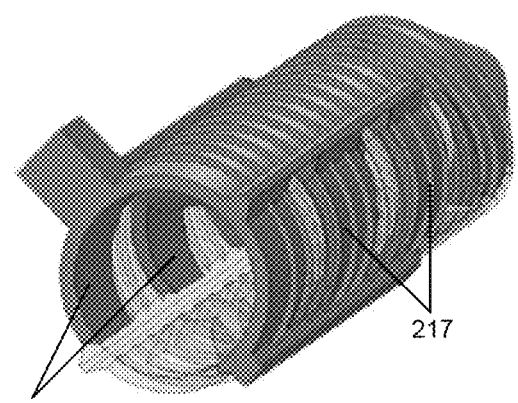
Figure 12D:
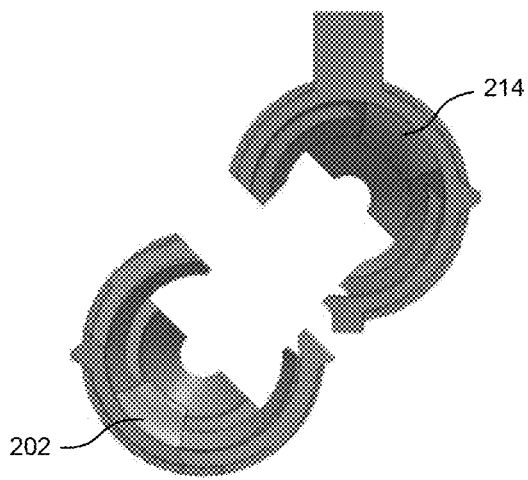

In a further embodiment, FIGS. 11A-C show sheath implant 170 having many similar aspects as sheaths 120 and 140 that will not be described again. Sheath 170 includes first body 184 and second body 172 attachable to one another to form a cannulated tubular sheath defining passage 180 extending along a longitudinal axis of the sheath for receiving an interference screw. As shown in FIG. 11B, proximal end 171 of sheath 170 may flare outward, which provides more interior space between the first and second bodies for easier screw starting. Sheath 170 does not include two bodies having an inner-outer configuration like sheaths 120 and 140. Instead, sheath 170 includes an attachment feature that allows first and second bodies 184, 172 to be positioned adjacent and in contact with one another, such that the two bodies form a continuous surface. The attachment feature couples the first and second bodies 184, 172 together and helps to prevent rotation of the second body. In the illustrated embodiment, the attachment feature includes interdigitating, interlocking ribs on each body that matingly engage one another. First body 184 includes two sets of a plurality of ribs 185 and a plurality of openings, each opening adjacent to at least one rib 185. The two sets of ribs 185 may be positioned on opposing lateral sides of the first body and be identical, as illustrated, though the positioning, size and shape of each rib relative to the others can be any as desired. Similarly, second body 172 includes two sets of a plurality of ribs 173 and a plurality of openings, each opening adjacent at least one rib 173. The two sets of ribs 173 may be positioned on opposing lateral sides of the second body and be identical, as illustrated, though the positioning, size and shape of each rib relative to the others can be any as desired. Ribs 185 of first body 184 are sized and configured to fit into the openings of second body 172. Likewise, ribs 173 of second body 172 are sized and configured to fit into the openings of first body 184.

As best shown in FIG. 11C, ribs 185 include at least one tab 185a projecting from a rib, such as projecting distally from side surface 194 near an end 196 and at least one wall or pocket 185b on opposing side surface 195 near lateral edge 191. Likewise, ribs 173 include at least one tab 173a projecting from a rib, such as projecting distally from side surface 174 near an end 178 and at least one wall or pocket 173b on opposing side surface 175, near lateral edge 179. Tabs 185a are sized and configured to be received within and interlocked with a corresponding wall or pocket 173b, and tabs 173a are sized and configured to be received within and interlocked with a corresponding wall or pocket 185b. Furthermore, with a screw positioned within the sheath and rotated, as discussed above, the tabs 173a, 185a and corresponding walls or pockets 173b, 185b may provide tactile feedback as the tabs are forced open as the screw separates the first and second bodies.

In the illustrated embodiment, each rib extends generally transverse to the longitudinal axis of sheath 170, and the ribs are centered at nine o'clock and three o'clock. However, the ribs may be positioned at various angles to the longitudinal axis, as described below.

In another embodiment, FIGS. 12A-D illustrate sheath implant 200, similar in many aspects to sheath 170. Sheath 200 includes first body 214 and second body 202 engageable to one another by interdigitating ribs on each body that matingly engage one another to define passage 230. First body 214 includes an optional cortical flange 252 and ribs 215, 217, and second body 202 includes ribs 203, 207. The cortical flange, or more than one flange, if present, could be positioned on one or both of the bodies 214, 202. Ribs 215 and ribs 217 of first body 214 are offset on the circumference of the sheath from each other. For example, ribs 215 and ribs 217 would not be centered at nine and three o'clock. Ribs 203 and ribs 207 are positioned in the same manner.

In the illustrated embodiment, sheath 200 defines a horizontal axis and a vertical axis, both axes transverse to a longitudinal axis extending along a length of the sheath. The horizontal and vertical axes define four quadrants, upper-left, upper-right, lower-left, and lower-right. With first and second bodies attached, ribs 203 and ribs 215 are each positioned in the upper-left quadrant, while ribs 207 and ribs 217 are each positioned in the lower-right quadrant. Although shown in this configuration, alternatively the ribs can be positioned such that the ribs are in the upper-right and lower-right quadrants.

Although the illustrated embodiment has been described above, the interdigitating ribs of the sheath can be positioned anywhere on the sheath that allows two or more sheath bodies to interlock and expand. The ribs can take many different shapes and sizes and can be angled in any manner, symmetrically, or non-symmetrically, on the sheath bodies. And further, the sheath could include three or more separate bodies instead of two as illustrated, which each body has two sets of ribs which can interdigitate with adjacent sets of ribs.

With the ribs positioned in the upper-left and lower-right quadrants, as shown, the offset positioning may help limit rotation of sheath 200 during insertion of the screw. For example, during insertion of a screw into sheath 200, the clockwise rotation of the screw may bias expansion of the sheath such that one side expands more than the other. The offset ribs compensate for a right side bias caused by the screw insertion in that the ribs are offset such that the upper right hand quadrant of the sheath, which is typically the location of the greatest forces caused by the rotation of the screw, is a solid portion with the interdigitated ribs now on either side of that location. In other words, the right side of the sheath includes more "rib material" to counteract the asymmetrical expansion. As a result, sheath 200 opens in a more uniform manner during clockwise rotation of the screw into the sheath.

Figure 13:
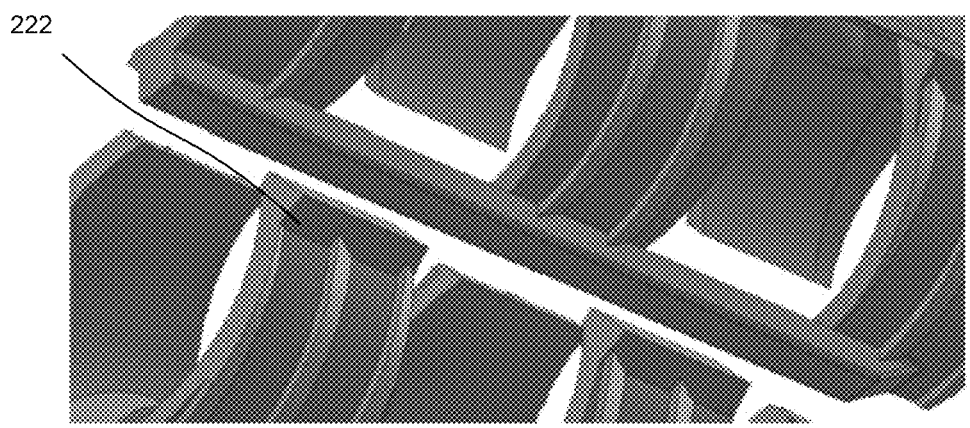
FIG. 13 is a close up of an interlocking feature of the implant of FIG. 12.

Continuing with this embodiment, as shown in FIG. 13, each rib may include a tab 222 at the free end of the rib. Tab 222 creates a stop surface between the ribs to assist in preventing full separation of first body 214 and second body 202. Additionally, if for example, only ribs 207 and 217 are expanding, tabs 222 will eventually be engaged, which forces ribs 203 and 215, positioned in a different quadrant, to start expanding to continue with the implantation procedure and help to equalize expansion between the two sets of interdigitating ribs.

Figure 14:
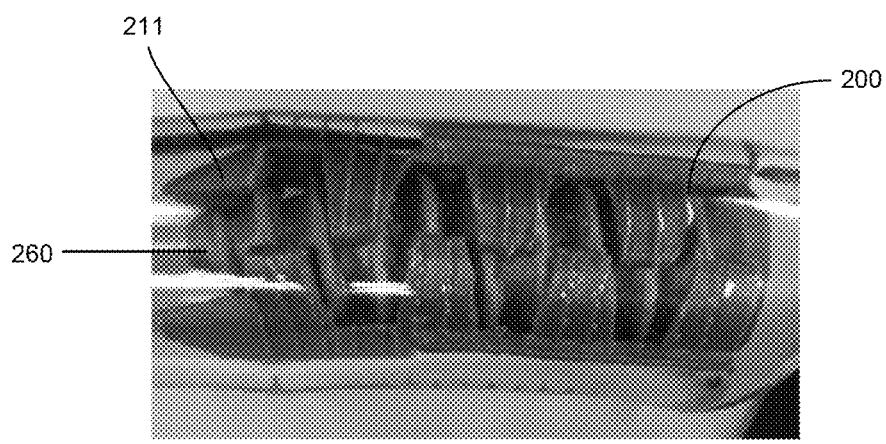
FIG. 14 is a top perspective view showing the implant of FIG. 12 in an expanded condition in conjunction with a fixation member within a simulated bone tunnel.

FIG. 14 shows sheath 200 in use with a fixation member, such as interference screw 260. With screw 260 inserted within sheath 200, the sheath is expanded to compress the graft and/or suture in between the outer surface of the sheath and the inner surface of the bone hole. Due to the asymmetrical positioning of the ribs, the sheath opens in a uniform manner Distal tip 211 of sheath 200 expands and can be designed to ensure that, as the screw becomes fully seated within the sheath, the sheath tip expands to reach a diameter similar to that of the mid-body of the sheath, which increases the surface area contact and may create additional fixation of the graft and/or suture, particularly near the tibial plateau. Each of the ribs described above allows the respective sheath to expand while maintaining connection between the two sheath bodies.

Continuing with this exemplary use, and as discussed above, typically an ACL graft includes four separate strand ends, which would be spaced around the outer surface of sheath 200 (or another sheath being used). Upon expansion of sheath 200, the ribs and tabs 222 promote even expansion along the length of the sheath such that fixation forces are imparted onto the strands of the graft along a greater amount of the longitudinal surface of the sheath. In this fashion, sheath 200 may impart greater fixation of the graft, and thus, a stronger soft tissue repair.

The above-referenced sheath implants can be utilized with a variety of instrumentation, and thus the implants and instruments can be organized into various systems and kits, certain exemplary embodiments of which are discussed below.

Figure 15A:
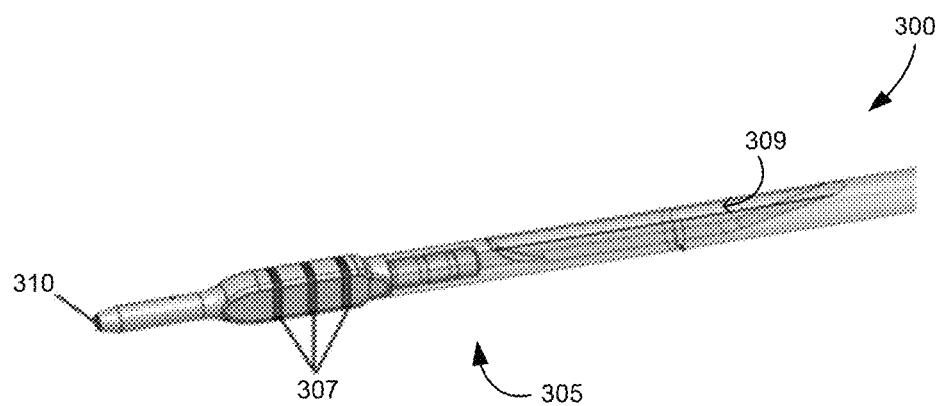
FIG. 15A is a side perspective view of a shaft portion of a dilator instrument according to an embodiment of the present disclosure.
Figure 15B:
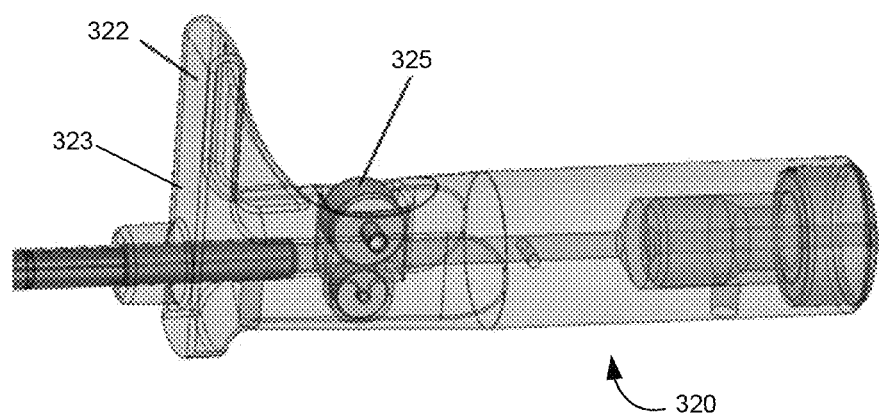
FIG. 15B is a side perspective view of the handle of the dilator, where the handle is translucent for purposes of illustration.
Figure 15C:
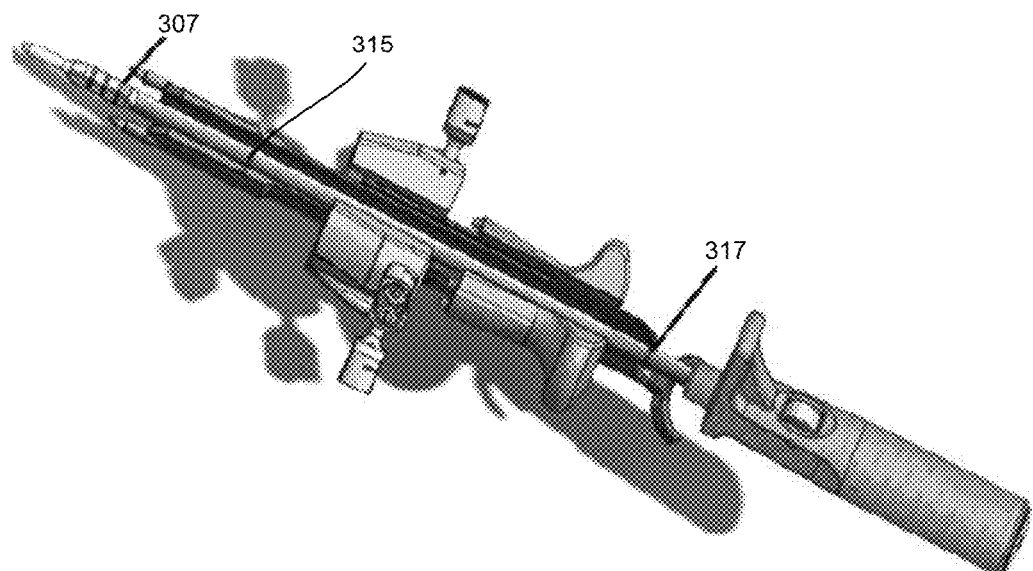
FIG. 15C is a top perspective view of the dilator in combination with a tensioner instrument according to an embodiment of the present disclosure.

In one embodiment of such instrumentation, FIGS. 15A-C show a cannulated dilator instrument 300 to be used during implantation of any of the sheaths described above, or in other surgeries without regard to the other embodiments of the present disclosure. Dilator 300 includes shaft 305 that extends along a longitudinal axis from handle 320 to cannulated distal tip 310. Referring to FIG. 15A, shaft 305 includes several indicators to provide a user, such as a surgeon, with an indication as to the proper depth of insertion of the dilator. For example, in the illustrated embodiment, shaft 305 includes calibration laser marks 307, near to distal tip 310, for indicating the insertion depth of dilator 300 relative to the bone. In the illustrated embodiment, three laser marks 307 are shown. However, in other examples, there may only be one laser mark indicating the appropriate depth of insertion of the dilator. In particular, in a system or kit with one or more sheaths having the same length, there may be one laser mark. Referring to FIG. 15C, shaft 305 includes laser mark 315 that corresponds to lines on a foot insert of a tensioner instrument, described in further detail below, to provide an indication of proper insertion depth of the dilator. Shaft 305 also includes relatively proximal laser mark 317 as yet another indication of appropriate insertion depth from another perspective.

Referring to FIG. 15B, dilator 300 includes handle 320 connected proximally to shaft 305. Handle 320 includes flange 322 projecting superiorly from the handle and including distal surface 323. Flange 322 allows a user to hit, for example with a mallet, distal surface 323 of the flange to move dilator 300 proximally for easier removal of the dilator.

Dilator 300 may also include a feature for controlling movement of a guide wire placed in the cannulation of the dilator. In one embodiment, shaft 305 may include recess 309 positioned between distal tip 310 and handle 320. Recess 309 may prevent a guide wire from getting stuck within dilator 300, prevent the guide wire from falling out, and allow for advancement of the guide wire inside the bone tunnel while removing the dilator. In an alternative embodiment, handle 320 includes wheel 325 positioned at least partially within the handle. Wheel 325 is rotatable and allows for movement and control of a guide wire placed within dilator 300. For example, wheel 325 can be rotated to retrieve the guidewire, prevent the guide wire from falling out, and advance guidewire inside the bone tunnel while removing dilator 300.

In some examples, a portion of shaft 305 adjacent distal tip 310 may have a larger diameter, for example of about 4 millimeters, to help ensure alignment within the bone tunnel.

Figure 16A:
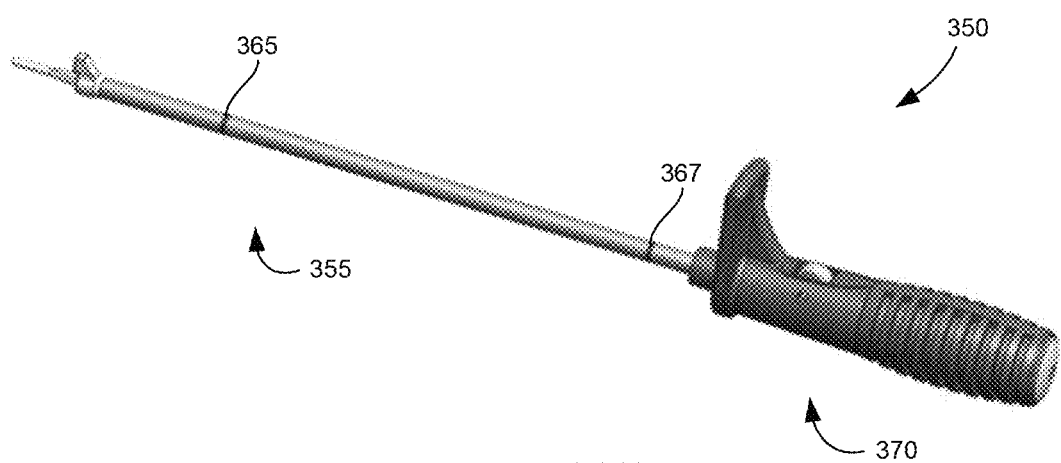
FIG. 16A is a side perspective view of an inserter instrument according to an embodiment of the present disclosure and FIG. 16B is a side perspective view of a shaft portion of the inserter, where the shaft is translucent for purposes of illustration.
Figure 16B:
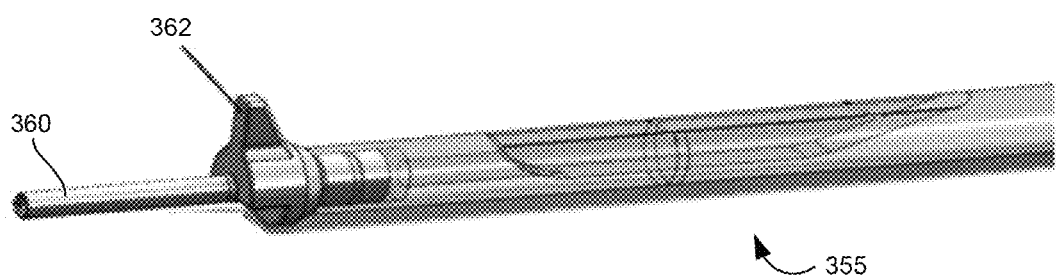

In another embodiment, FIGS. 16A-B show cannulated inserter instrument 350 to be used in connection with any of the above sheaths or without reference to any other embodiments of the present disclosure. Inserter 350 includes shaft 355 connected to handle 370. Shaft 355 includes laser marks 365 and relatively proximal laser marks 367 identical to laser marks 315 and 317 of dilator 300, respectively. Shaft 355 includes stop flange 362 positioned near cannulated distal tip 360. Stop flange 362 prevents over insertion of inserter 350 into the bone. Handle 370 of inserter 350 includes identical features to handle 320 of dilator 300, which will not be described again. Furthermore, inserter 350 may include a wheel identical to wheel 325 of dilator 300, or in an alternative embodiment, the inserter may include a recess identical to recess 309 of the dilator.

Figure 16C:
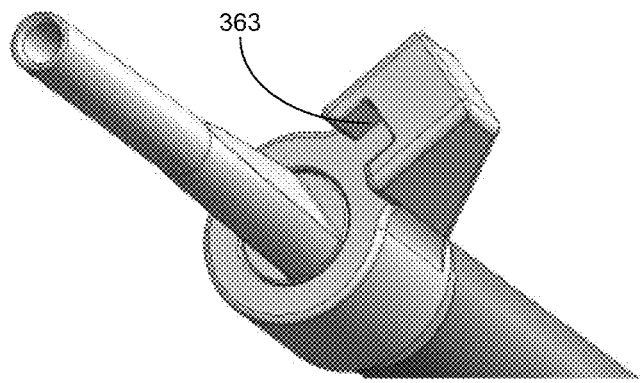
FIG. 16C is an enlarged view of a distal end of an alternative embodiment of the inserter, according to another embodiment of the present disclosure.
Figure 16D:
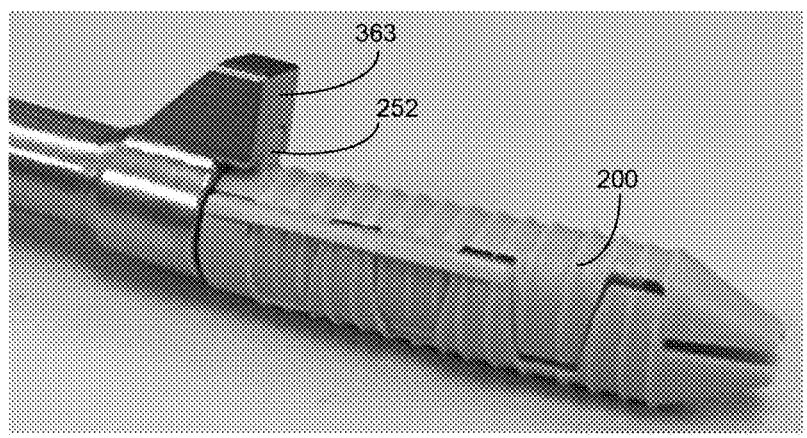
FIG. 16D is a schematic view of the inserter of FIG. 16C in conjunction with an exemplary implant of FIG. 12, according to an embodiment of the present disclosure.

As shown in FIGS. 16C-D, stop flange 362 may also include overhang 363 within which a cortical flange of a sheath, such as cortical flange 252 of sheath 200, sits to help ensure that the smaller sheath flange remains flush with the bone surface. Furthermore, overhang 363 may protect the sheath flange during insertion and assist the surgeon in maintaining a desired orientation of the sheath during insertion.

Figure 17A:
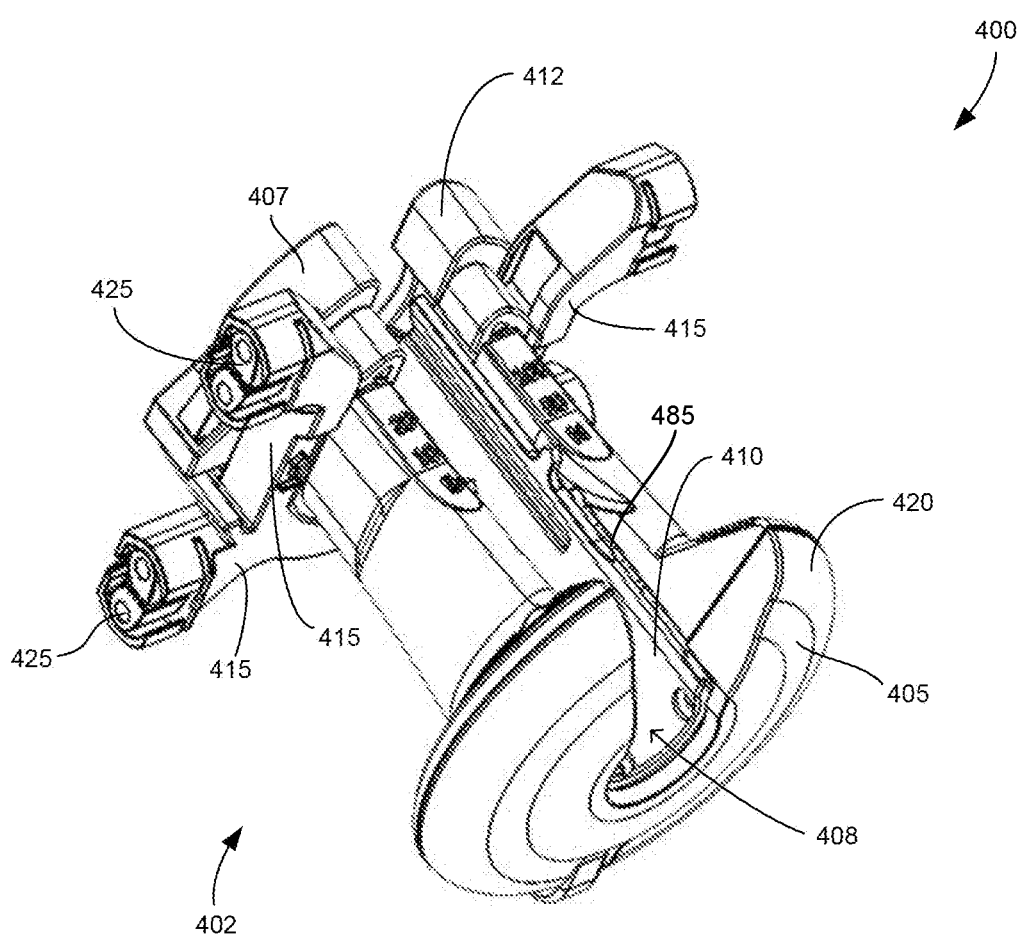
FIGS. 17A-B are side perspective views of a tensioner instrument according to an embodiment of the present disclosure.
Figure 17B:
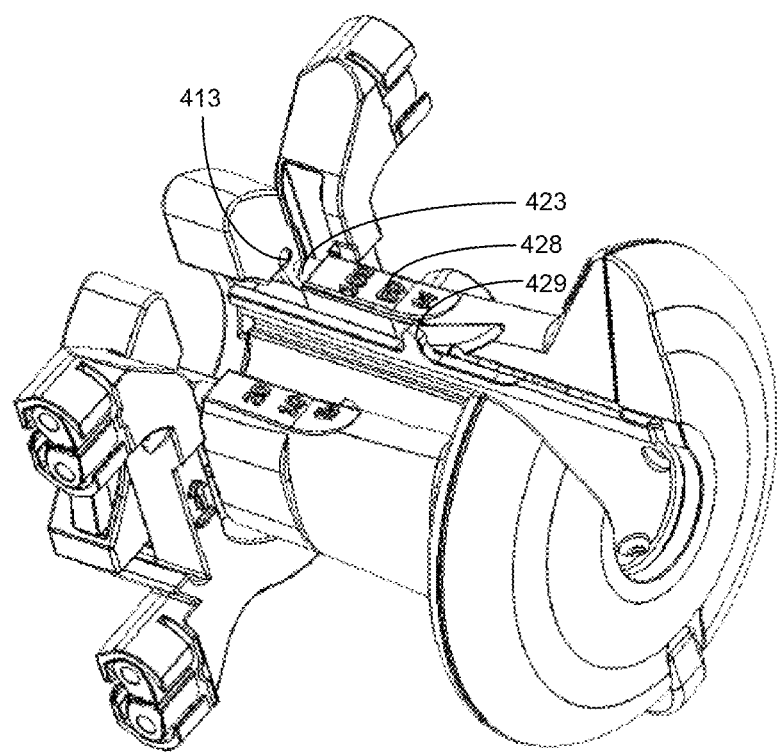
Figure 17C:
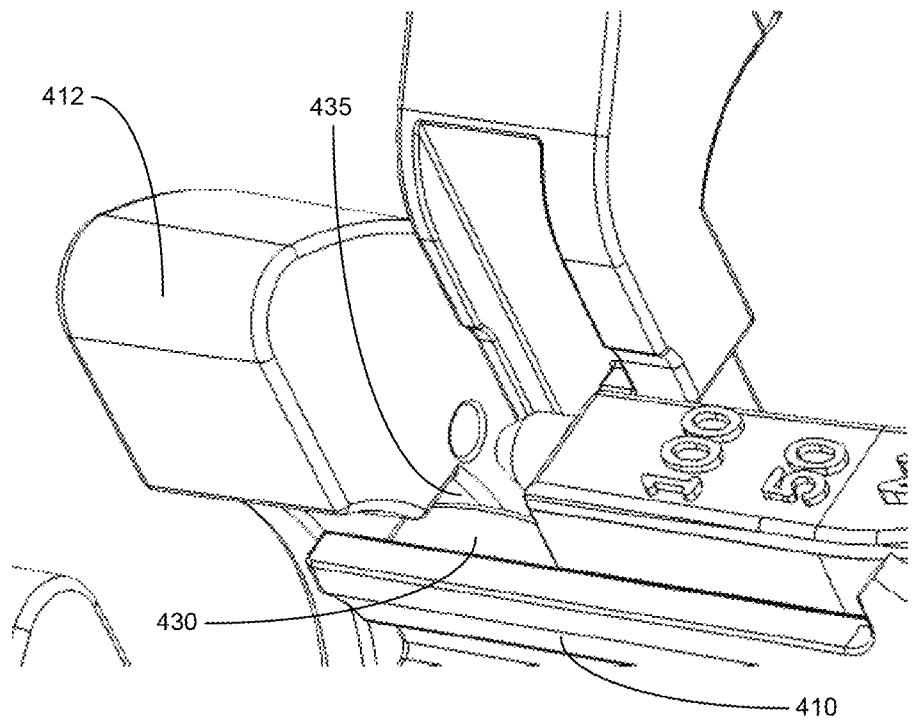
FIG. 17C is an enlarged view of the universal joint of the tensioner of FIGS. 17A-B.

The present disclosure also includes a tensioner instrument. The tensioner can be used to tension a graft and/or suture that is being positioned relative to bone. In one embodiment, FIGS. 17A-C show tensioner instrument 400 for tensioning suture and/or soft tissue, according to an embodiment of the present disclosure. Tensioner 400 includes body 402 extending along a longitudinal axis from proximal end 405 to distal end 407. Body 402 includes actuating mechanism or handle 420 at proximal end 405 and a plurality of arms 415 spaced apart from one another and extending radially outward of the body. Each arm 415 includes a cleat 425 for securing suture and/or soft tissue, as will be described in detail below. In the illustrated embodiment, there are four arms 415 on body 402, with two arms positioned on each lateral side of the body. However, in other examples, there may be more or less of arms 415.

Additionally, body 402 defines a pathway extending along a length of the body, such as channel 408. Channel 408 has a perimeter about its central axis that is not fully enclosed within body 402 at any location along its central axis so that it is open in the superior direction. Base 410 is a generally "U-shaped" member positioned within channel 408 and extending at least a majority of the length of the channel. Body 402 is generally symmetrically shaped on each lateral side of the longitudinal axis extending the length of the body. In this manner, certain details may be described and shown in the figures with reference to one side, but it is to be understood that the same or similar features are present on the opposing lateral side of the body.

Handle 420 is moveable between a first position in which the handle is connected to member 412 by a securing mechanism and a second position in which the securing mechanism is disengaged and the handle is moved proximally relative to base 410. As shown in FIG. 17B, one such securing mechanism are engageable coupling members, such as projection 423 received within hole 413 on annular member 412 which is connected to or integral with arms 415. In other examples, there may be more or less of projections and corresponding holes. Additionally, other securing mechanisms that also allow for proximal movement of handle 420 are envisioned.

Handle 420 has a generally round shape with a diameter that is larger than the diameter of the body adjacent the handle to allow for easier gripping of the handle by a user. Furthermore, handle 420 is spring-actuated. The spring 485 may be positioned proximally of arms 415 within body 402, though it can be positioned elsewhere so long as it maintains its functionality, such as, in other examples, the spring may be positioned distally of arms 415. Body 402 may include tension gauge 428 and/or indicator 429 to allow the user to know how much force is applied to the spring, and thus the soft tissue and/or suture. Force indicator 429 may project superiorly from base 410 near gauge 428 such that as handle 420 moves relative to the base, the force indicator is positioned adjacent to the reference point indicating the amount of force that is applied with the handle in that particular position.

As an alternative to grabbing handle 420, tensioner 400 may include other mechanisms to generate tension, such as a worm gear drive (not shown). Such a drive may include a rotating knob below channel 408, which can be utilized to drive proximal end 405 further proximally to generate tension.

Continuing with this embodiment, and as best shown in FIG. 17C, base 410 and annular member 412, to which arms 415 are attached, form a ball and socket arrangement, such that the two members are fully pivotable about the connection point. Base 410 includes convex surface 430 on an outer surface of the base. Annular member 412 includes a complementary concave surface 435 on an inner surface for receiving convex surface 430. In this manner, because arms 415 are connected to annular member 412, the arms are also freely moveable relative to base 410. As a result, arms 415 are connected by a universal joint to base 410 and are laterally adjustable relative to the base.

Figure 18:
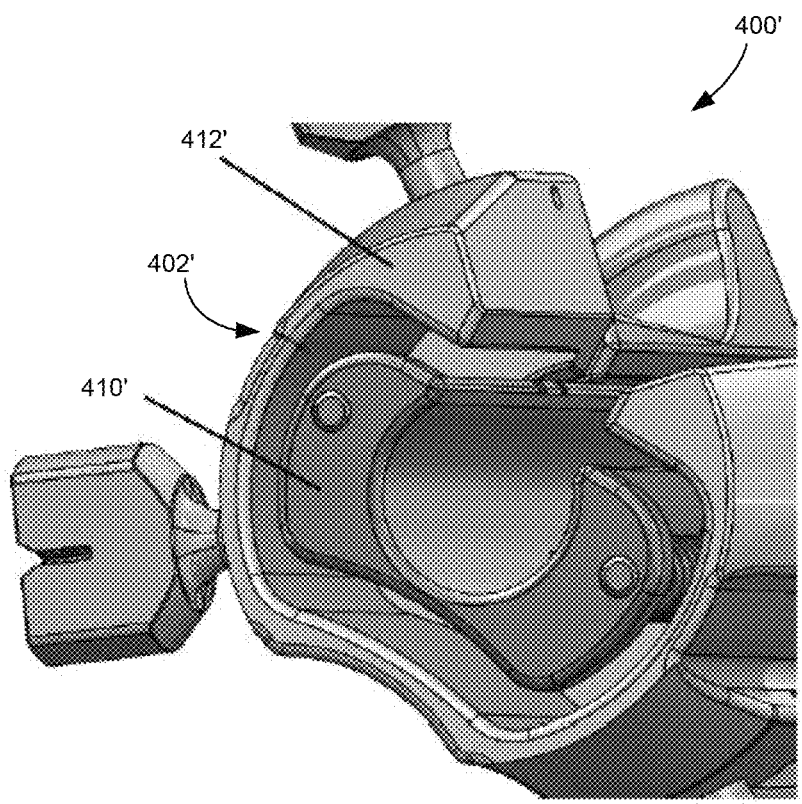
FIG. 18 is a rear perspective view of a tensioner instrument according to an embodiment of the present disclosure.

In an alternative embodiment, as shown in FIG. 18, rather than utilizing the ball and socket arrangement, as described above, tensioner 400' may include a space between base 410' and annular member 412' of body 402' to allow for freedom of movement of the arms with respect to the base.

Figure 19A:
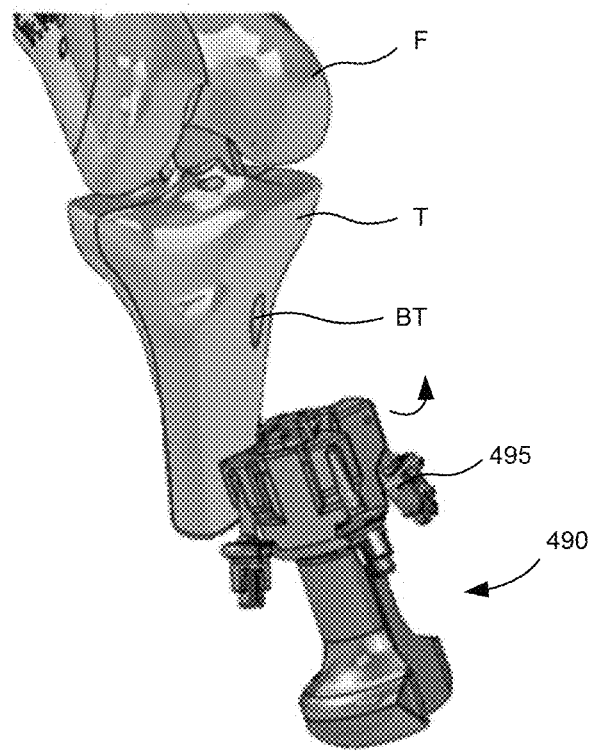
FIGS. 19A-B are schematic perspective views of a tensioner instrument according to another embodiment of the present disclosure, positioned relative to a tibia and femur.
Figure 19B:
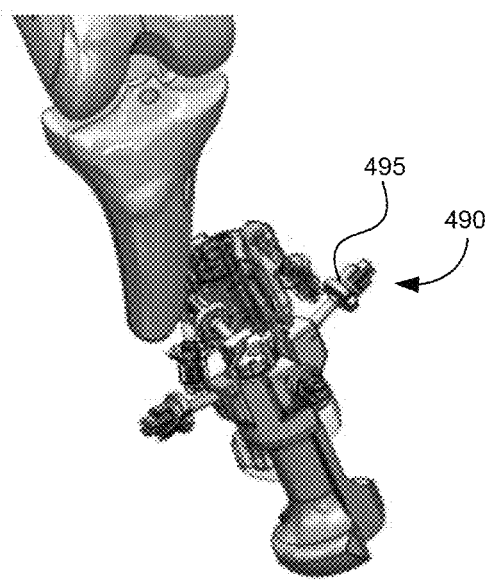

In another embodiment, as shown in FIGS. 19A-B, tensioner 490 may include foldable arms 495, which move from a folded position (FIG. 19A), in which the arms extend proximally, to a deployed position in which the arms extended radially outward of the tensioner body. FIG. 19B shows the translation involved in transitioning the tensioner from a folded position to a deployed position. The folded position (FIG. 19A) allows the tensioner to remain stabilized against the patient's skin while sutures and/or grafts are loaded to the tensioner in a roughly equal distance/length configuration. The outward extension of the arms creates the separation from the patient's skin necessary to safely tension the sutures and/or grafts without stressing the skin incision. The arms may be actuated by a biased spring, a camming action, or the like. For example, the arms may be biased towards the folded configuration such that, upon the release of tension the arms fold back proximally to maintain organization of the various sutures and/or soft tissue and the various instrumentation. Alternatively, the arms could be biased in the radial direction to allow for simplified extension of the arms to easily generate the separation of the sutures and/or soft tissue. Furthermore, the tensioner may include specifically angled contact surfaces, angled such that the tensioner can rest flush against the skin and underlying bone and anatomy. This contouring of the tensioner body may be useful to provide stable seating of the tensioner against the patient through surgery, in particular, for example, while loading sutures and/or grafts to the tensioner as well as after the tensioner has been attached to the suture and/or soft tissue but before tensioning occurs.

Figure 20A:
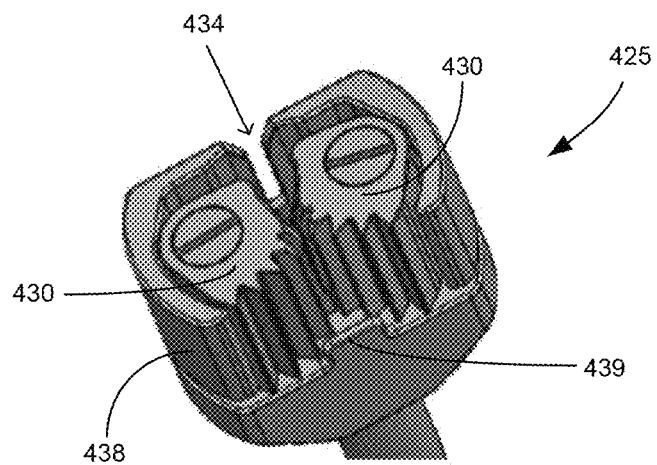
FIGS. 20A-B are perspective views of a cleat according to an embodiment of the present disclosure.
Figure 20B:
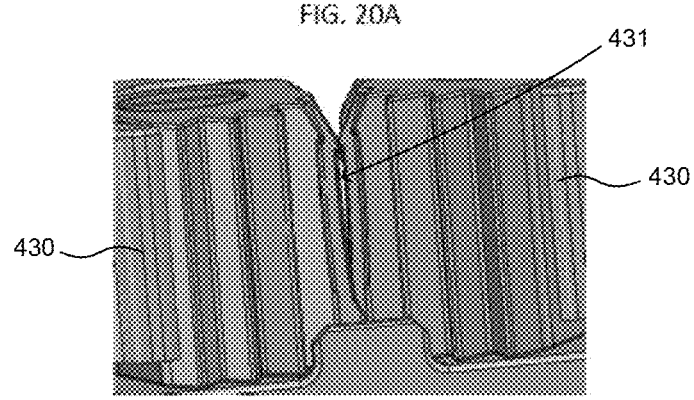
Figure 20C:
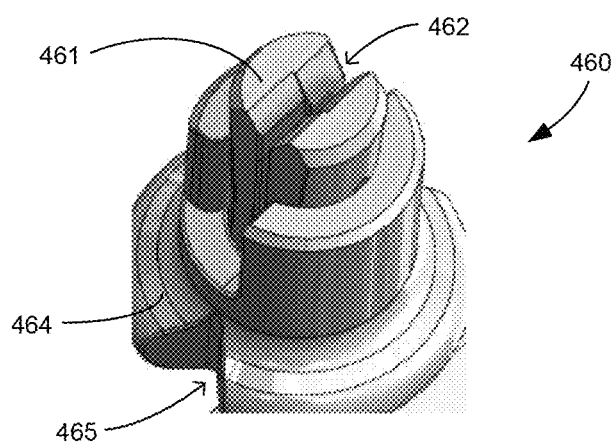
FIGS. 20C-D are perspective views of a cleat according to another embodiment of the present disclosure.
Figure 20D:
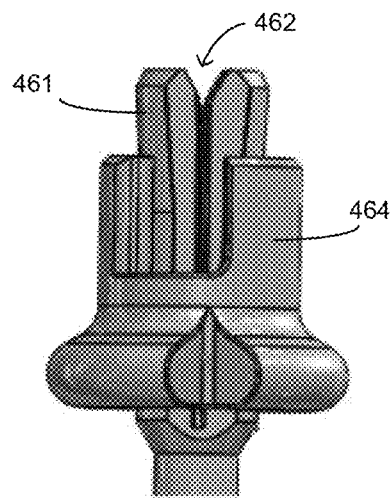
Figure 20E:
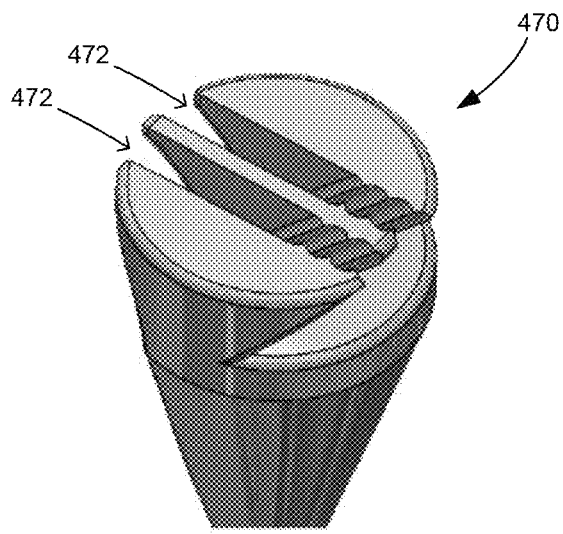
FIGS. 20E-F are perspective views of a cleat according to yet another embodiment of the present disclosure.
Figure 20F:
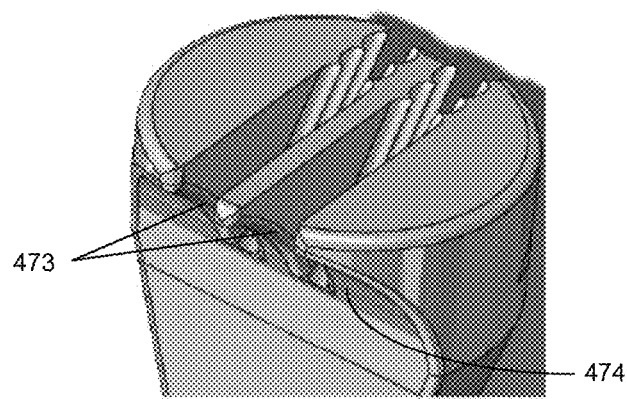

Additionally, although any type of cleat known in the art can be used with arms 415, FIGS. 20A-F illustrate a few examples. Referring to FIGS. 20A-B, double cam cleat 425, shown above in FIG. 17, includes two cams 430 positioned adjacent each other. As suture is loaded through front 434 of cleat 425, cams 430 are moved apart from one another. Living spring 438 provides spring resistance to force cams 430 back toward one another. Cams 430 have an increasing radial dimension, which provides for more interference as suture becomes tensioned. Further, cleat 425 includes at least one step 439 to prevent suture from getting stuck beneath cams 430. Additionally, as best seen in FIG. 20B, cams 430 have a small pocket of space or slot 431 between them which provides the user with a feedback that the sutures were properly in place between the cams. Referring to FIGS. 20C-D, cleat 460 includes body 461 having slot 462 with a tortuous path and a slider 464 translatable up the body. Slider 464 includes cut-out 465 to allow access to slot 462. When suture is loaded into slot 462, slider 464 is positioned in an initial position. After the suture is loaded, slider 464 is translated upward toward an end of the cleat, which squeezes the suture within slot 462. Referring to FIGS. 20E-F, cleat 470 includes two cuts or slots 472 angled in a "V-shape" having no radius or gap at the bottom of the cut. Additionally, cleat 470 includes curved portions 473 that extend beyond front 474 of the cleat and facilitate easier loading of the suture into each respective cut 472. As suture is loaded in front 474 of cleat 470, the suture is forced deeper into cuts 472 due to the shape of the cut.

Figure 21A:
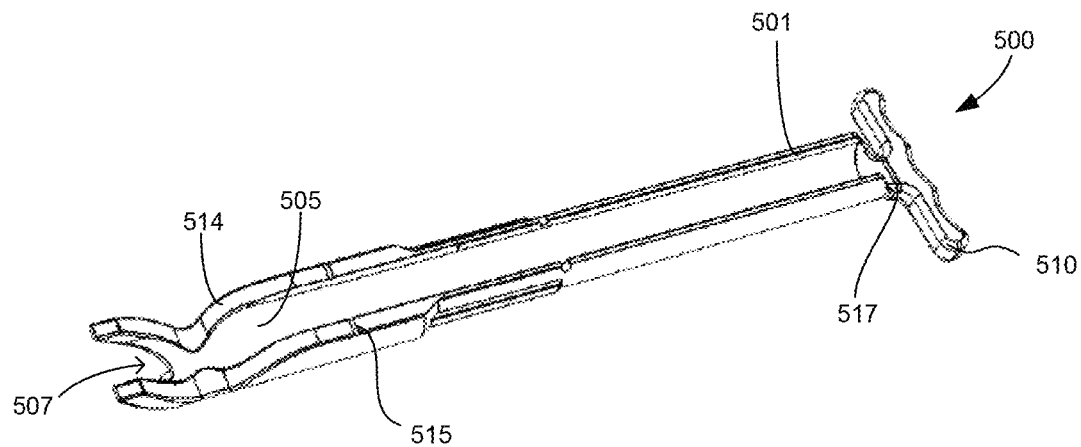
FIG. 21A is a side perspective view of a foot component according to an embodiment of the present disclosure.
Figure 21B:
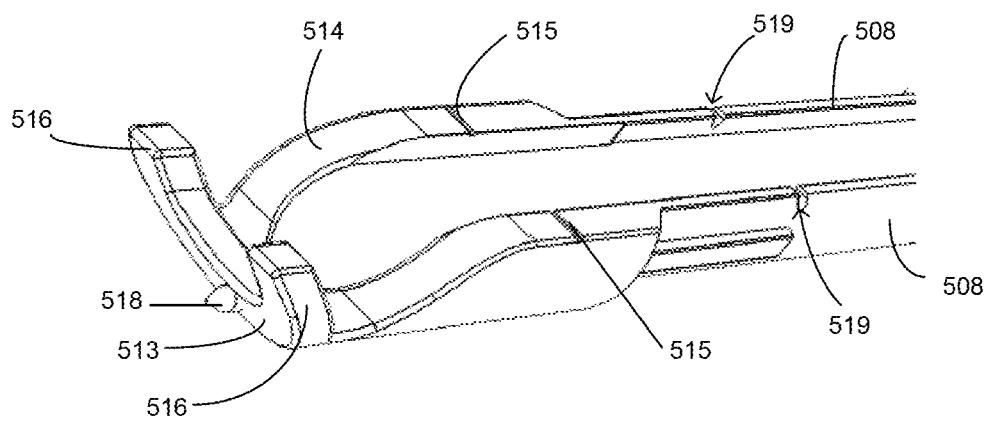
FIG. 21B is an enlarged view of a distal end of the foot of FIG. 21A.

In another embodiment, FIGS. 21A-B show a foot component 500 to be used with tensioner 400 according to another embodiment of the present disclosure. As described below, tensioner 400 can be used with various modular foot inserts or with no foot insert, depending on the preference of the user. Foot 500, when utilized, can be positioned within body 402 on base 410 and extend along a longitudinal axis extending the length of the foot. Foot 500 includes a generally concave inner surface 505 defining channel 507 to allow additional instrumentation to fit within the foot. At proximal end 501, foot 500 includes bar 510 to allow a user to push the bar with one or two fingers. Furthermore, bar 510 includes indents for ergonomic gripping of the bar. At distal end 514, foot 500 includes two flanges 516 forming a "U-shape." Flanges 516 are angled with respect to a central axis of foot 500. This angle can be from 0-90 degrees, and in particular, can be between 35 and 65 degrees to allow for better alignment with the trajectory of the tibial tunnel. Additionally, spike 518 projects outwardly from distal end surface 513. Proximal to flanges 516, the distal end portion of the channel 508 has a shallow shape to allow passage of the bottom sutures and/or soft tissue to extend to the lower cleats.

Moreover, foot 500 can include laser marks 515 relatively near distal end 514 that align with laser marks 315 of dilator 300 and/or identical laser marks on inserter 350. Similarly, foot 500 can include laser marks 517 near proximal end 501 for alignment with laser marks 317 of dilator 300 and identical laser marks of inserter 350. These laser marks provide a user with an indication of proper depth of the dilator and inserter with respect to the bone through the foot connection.

Furthermore, foot 500 includes divots 519 on each lateral wall 508 having a superiorly facing curved inner surface adapted to receive pins on an obturator, described below.

Figure 22:
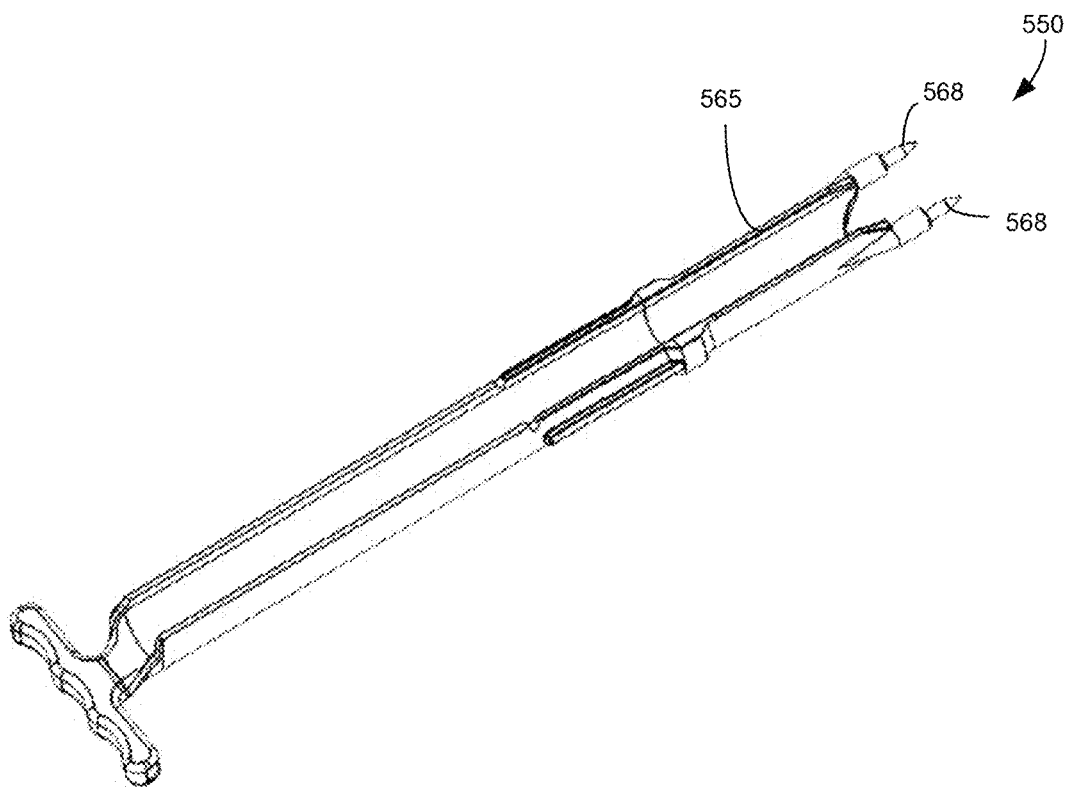
FIG. 22 is a side perspective view of a foot component according to another embodiment of the present disclosure.

In another embodiment, FIG. 22 shows foot 550 which is similar in many aspects to foot 500, described above. Similar features will not be described again. Distal end 565 of foot 550 includes two lateral spikes 568 projecting distally from the distal end of the foot.

Figure 23:
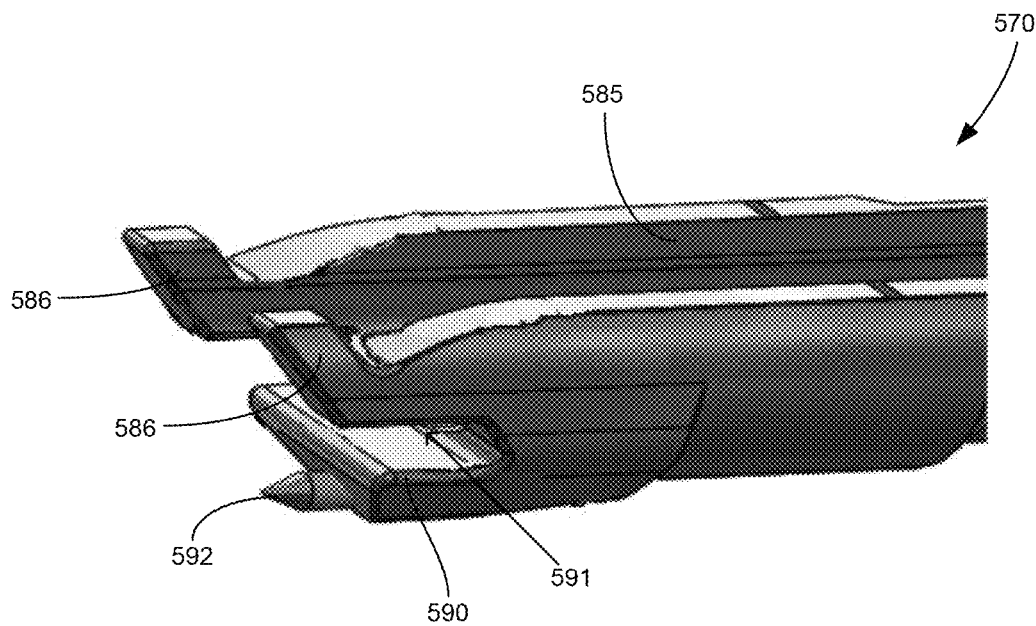
FIG. 23 is an enlarged view of a distal end of a foot component according to yet another embodiment of the present disclosure.

Another embodiment of a foot for use with tensioner 400 is shown in FIG. 23. Foot 570 includes two lateral flanges 586 at distal end 585 and platform 590 from which spike 592 projects distally. Foot 570 includes slot 591 that allows sutures and/or grafts to exit downward toward the lower cleats of the tensioner.

In use, where for example, 4 graft strands, with suture tails extending from each of the graft strands, are utilized, foot 500 allows all four sutures and/or grafts to be positioned within U-shaped channel 507. Alternatively, foot 550 allows two sutures and/or grafts to be positioned above spikes 568 and two sutures and/or grafts to be positioned below spikes 568. As a further alternative, foot 570 has an angled platform 590 like foot 500 but allows the upper two sutures and/or grafts to be positioned in the U-shaped channel and the two lower sutures to be positioned within slot 591.

Figure 24A:
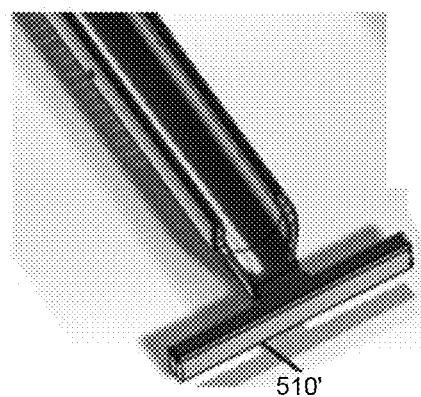
FIG. 24A is a front perspective view of a handle for use with any of the feet of FIGS. 21-23 according to an embodiment of the present disclosure.
Figure 24B:
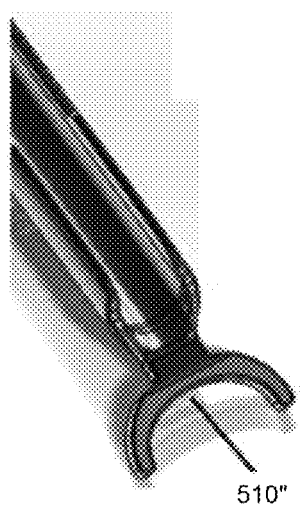
FIG. 24B is a front perspective view of a handle for use with any of the feet of FIGS. 21-23 according to another embodiment of the present disclosure.
Figure 25A:
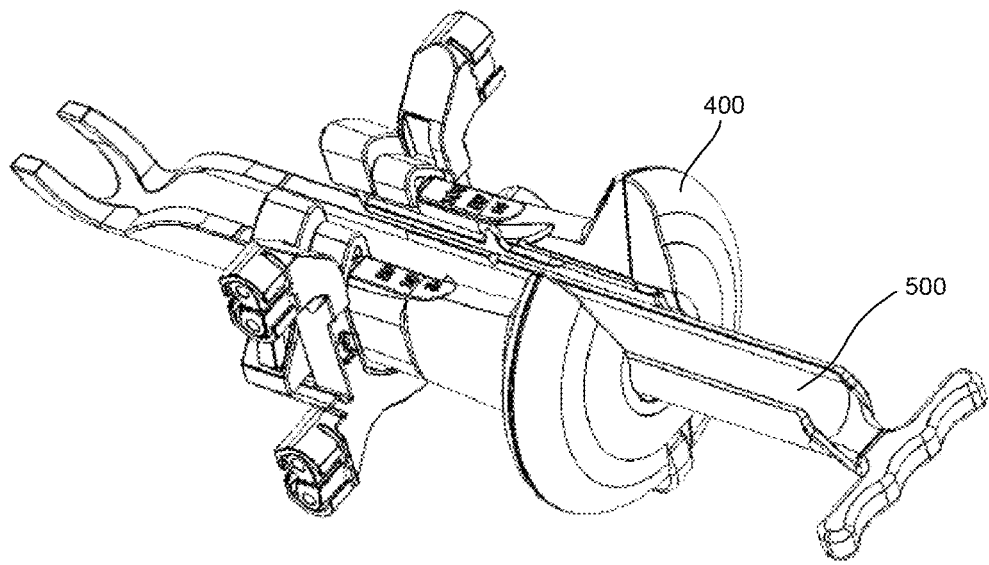
FIG. 25A is a side perspective view of the foot of FIG. 21A in combination with the tensioner of FIG. 17 according to an embodiment of the present disclosure.
Figure 25B:
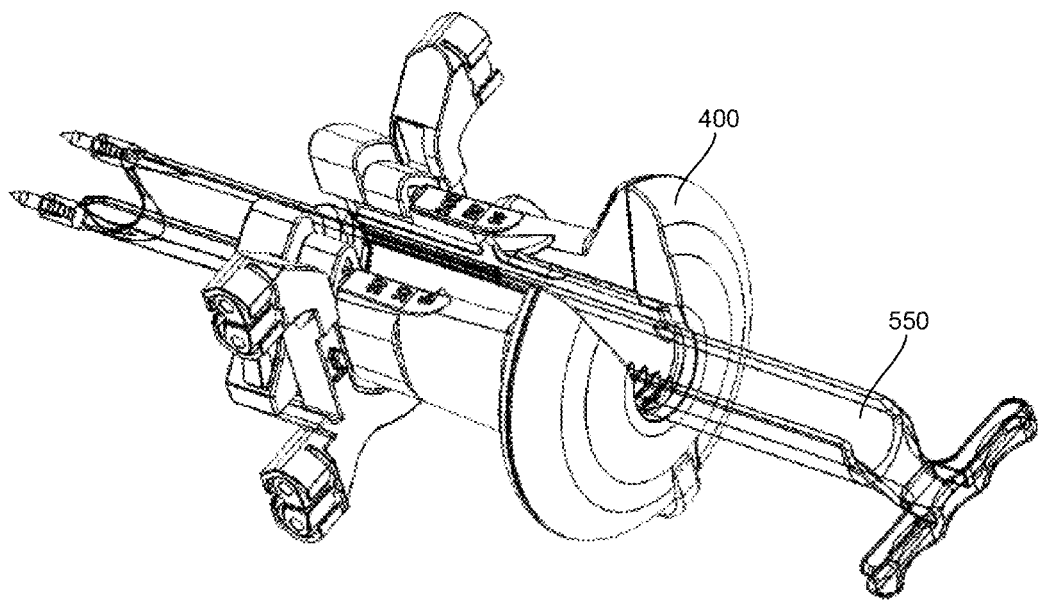
FIG. 25B is a side perspective view of the foot of FIG. 22 in combination with the tensioner of FIG. 17 according to another embodiment of the present disclosure.

Distal ends 514, 565, 585 of feet 500, 550, 570 are formed to allow the foot to engage the bone. Furthermore, the feet are designed so that at the point that the distal end contacts and engages the bone, arms 415 of tensioner 400 should be the appropriate distance from the bone to allow even tensioning on the sutures. Furthermore, although feet 500, 550 are shown with bar 510, other bars are possible including bar 510' in FIG. 24A and bar 510" in FIG. 24B. For the sake of illustration, FIG. 25A shows tensioner 400 in conjunction with foot 500, and FIG. 25B shows tensioner 400 in conjunction with foot 550.

Figure 26A:
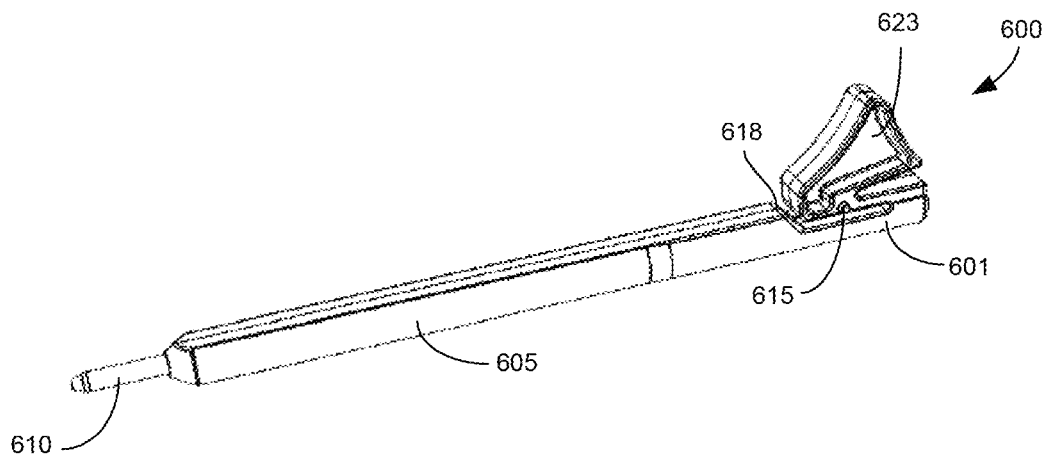
FIG. 26A is a side perspective view of an obturator instrument according to an embodiment of the present disclosure.

In a further embodiment, FIG. 26A shows cannulated obturator instrument 600 designed to be used in conjunction with a foot, such as foot 500 or foot 550 and tensioner 400.

Obturator 600 includes shaft 605 extending along a length of the obturator and terminating in distal tip 610. Distal tip 610 may have, for example, a diameter of about 2-5 millimeters and a length of about 12-30 millimeters. At proximal end 601, shaft 605 includes pins 615 extending outward from the shaft 605 that engage divots 519 on foot 500 to prevent movement of obturator 600 when the pins are engaged with the divots. Shaft 605 includes trigger 623 that controls movement of pins 615 inward and outward. Obturator 600 may be cannulated or not.

Figure 26B:
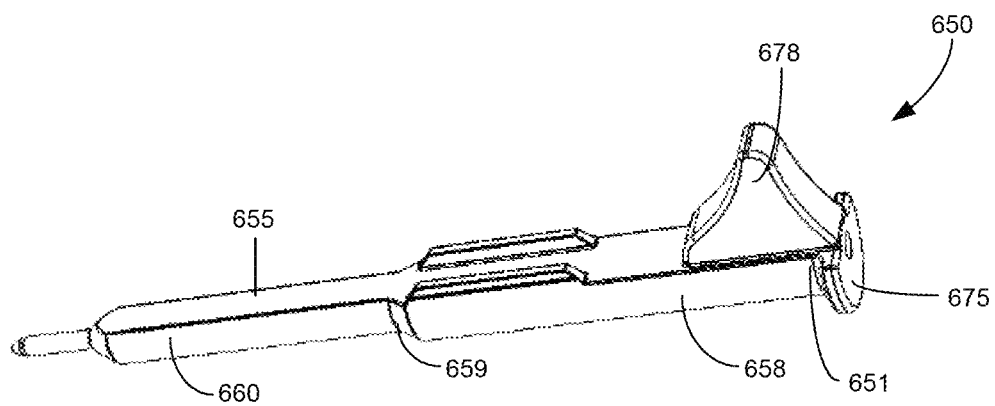
FIG. 26B is a side perspective view of an obturator instrument according to another embodiment of the present disclosure.

In yet another embodiment, FIG. 26B shows obturator instrument 650 designed to be used with tensioner 400 but without a foot. Obturator 650 includes shaft 655 that includes proximal section 658 and distal section 660, with tapered transition section 659 extending between sections 658 and 660. In the illustrated embodiment, proximal section 658 has a diameter that is larger than the diameter of distal section 660, so that the proximal section of the shaft can fit relatively securely within base 410 of tensioner 400. Although, in other embodiments, the diameter of shaft 655 can be a constant diameter, the same or similar to the diameter of proximal section 658. At proximal end 651, shaft 655 includes rounded shoulder 675 having a diameter greater than the diameter of proximal section 658 of the shaft. Additionally, obturator 650 includes handle 678 extending superiorly on shaft 655 to allow a user to move the obturator. Obturator 650 may be cannulated or not.

Obturators 600 and 650 may further include additional laser marks corresponding to laser marks on a proximal end of the tensioner body to ensure proper alignment of the obturator with respect to the tensioner, and ultimately proper alignment of the tensioner with respect to the bone.

Figure 27A:
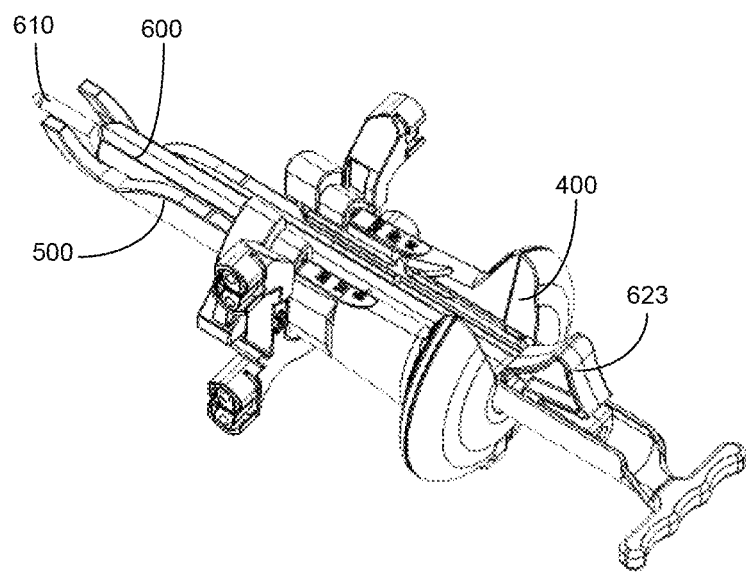
FIG. 27A is a side perspective view of the tensioner of FIG. 17 in combination with the foot of FIG. 21A, and the obturator of FIG. 26A, according to an embodiment of the present disclosure.

FIG. 27A shows tensioner 400, foot 500, and obturator 600 for use in a system according to an embodiment of the present disclosure. Foot 500 is placed within base 410 of tensioner 400, such that distal end surface 513 of the foot is about 50 mm, or another pre-set distance from a distal end of annular member 412 of tensioner body 402. Obturator 600 is positioned within foot 500 such that pins 615 of the obturator are received within divots 519 of the foot. With pins 615 in divots 519, the obturator is in the proper alignment. In this manner, with obturator 600 positioned within foot 500, or foot 550, pins 615 are positioned within divots 519 in an initial position of the obturator. In this configuration, distal tip 610 of obturator 600 is further distally than foot 500.

In use, at least two graft strands can be inserted into a bone tunnel, such as a tibial tunnel. The graft can have suture secured to it, so that the suture engages with the tensioner, or the graft itself can engage with the tensioner. As discussed above, in the ongoing example of an ACL graft, the graft typically has four strands, optionally with a suture extending from each strand, such that each cleat on the tensioner engages a suture and/or graft strand. Distal tip 610 of obturator 600 is placed inside the bone tunnel, in between the four graft strands, to provide proper alignment of the tensioner to the bone tunnel. Trigger 623 is actuated, so that pins 615 are removed from divots 519 of the foot. Tensioner 400 and foot 500 are moved distally toward the bone until spike 518 of the foot engages the bone around the tibial tunnel. At this point, the tensioner body is the desired distance from the edge of the bone tunnel, and in particular, about 50 millimeters. The sutures are then attached to cleats 425 of the tensioner, and the dilator can be removed. Because the tensioner body is a set distance from the tunnel, the sutures are loaded onto the cleats with relatively similar, but not necessarily equal, tensions. The securing mechanism, i.e. projections 423 in holes 413, helps to keep cleats 425 stable as the sutures are loaded on the cleats. Handle 420 of tension 400 is moved proximally, releasing the securing mechanism, i.e. projections 423 from holes 413. Arms 415 of the tensioner are freely movable in any direction relative to base 410 and foot 500, such that there is a universal joint formed from the convex surface of base 410 and the concave surface of inner surface 435 of annular member 412, to which arms 415 are attached. As arms 415 move relative to base 410, the tension on each of the graft strands simultaneously adjusts to substantially equal tension. In other words, the different tensions on each of the sutures and/or soft tissue strands creates the overall net force on the arms 415 to move the arms relative to the base 410 via the universal joint, which thereby equalizes the tension on each suture and/or soft tissue.

Next, typically, while maintaining tension on the graft, dilator 300, with a guide wire positioned through its cannulation, is positioned within foot 500 and aligned with laser marks 315 and 317 of the dilator aligning with laser marks 515,517 of the foot, respectively. The dilator is then used to compress the grafts and increase the size of the opening. The dilator is removed, and the inserter 350 having an expandable sheath, similar or identical to any of the sheaths described above, and optionally a guide wire is inserted into or maintained within the tensioner. The sheath is positioned within the bone, and the inserter removed. At this point, the graft strands should all be under substantially equal tension and the sheath should be in position in the tibial bone. Next, a fixation member, such as an interference screw, is inserted over the guide wire, and torqued into engagement with the sheath, which expands the sheath for further engagement into the sutures and/or grafts and the surrounding bone tunnel.

Alternatively, divots 519 may be shaped differently to allow alternative usage of the obturator within the foot. For example, the divot may be in the shape of an elongated slot (not shown) to allow the obturator to slide from a distal to a proximal position relative to the foot without the use of trigger 623.

Figure 27B:
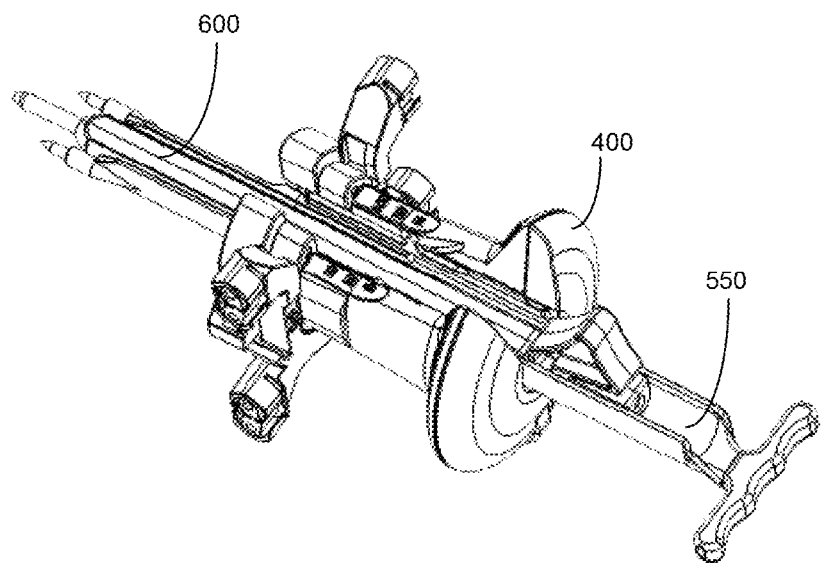
FIG. 27B is a side perspective view of the tensioner of FIG. 17 in combination with the foot of FIG. 22, and the obturator of FIG. 26A, according to another embodiment of the present disclosure.

FIG. 27B shows tensioner 400, foot 550, and obturator 600, which can be used in the same manner as described above with reference to the system including foot 500.

Figure 28:
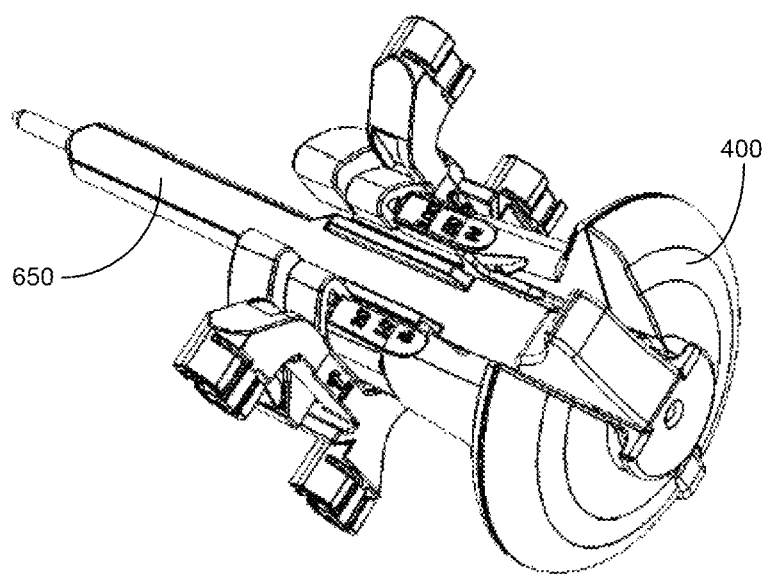
FIG. 28 is a side perspective view of the tensioner of FIG. 17 in combination with the obturator of FIG. 26B according to another embodiment of the present disclosure.

FIG. 28 shows tensioner 400 and obturator 650, without the use of a foot, for use in a system according to an embodiment of the present disclosure. Because there is no foot to provide an indication of the appropriate distance of the tensioner from the bone, the sutures may attach to the cleats of the tensioner at a sharp angle, which may cause the suture to intersect with the body, such as the skin and/or bone around the tibial tunnel. Obturator 650 almost acts as a temporary foot against the graft strands as opposed to the bone to ensure that the tensioner is the proper distance from the bone tunnel. Additionally, obturator 650 helps to maintain proper alignment with the tunnel and maintain roughly equal distances to each of the cleats from the tunnel. Further, shoulder 675 acts as a stop against handle 420 of tensioner 400 to prevent the obturator from moving too far distally.

The present disclosure may also include various systems and kits based on the various instruments, implants and devices discussed above. While it is envisioned that these various devices, implants and instruments may be utilized, packaged, sold, or designed in any number of systems and kits, a few representative embodiments will be discussed in detail below.

In another embodiment, the present disclosure can include a kit which can be packaged in a single package as a system or in multiple packages that can be selected as needed by the operator to form a system. For example, such a kit may include at least one sheath, at least one fixation member, and at least one inserter instrument. If the kit includes more than one sheath and/or fixation member, the plurality of sheaths and/or fixation members can vary in length, width, thread count, outer or inner textures (e.g., teeth, flanges etc. as discussed above), or the like, from which an operator can select the best types and sizes for a particular surgical procedure. Such a kit may also include a tensioner instrument, an obturator instrument, and/or the like. Any combination of implants, instruments and components may also be included in a single package or in separate packaging which are later brought together as a kit.

In yet another embodiment, a kit of the present disclosure may be specific to, for example, ACL reconstruction, and would include at least one sheath, at least one fixation member, at least one inserter instrument, at least one obturator, and at least one tensioner instrument, and/or any related components or instruments such as K-wires, femoral and tibial sheaths and fixation members, and the like.

In yet another embodiment, a kit of the present disclosure may include at least one sheath and at least one disposable arm 415 to ensure cleats 425 function properly for each surgery. The arms 415 are attachable to the tensioner, and the desired number of arms can be attached thereto. For example, each arm 415 may be an independent structure engageable with the tensioner independently. Thus, continuing with this example, the tensioner may have attachment locations for up to eight arms and the operator can attach the number of arms desired, up to eight. The fixation member may be packaged separately due to their various sizes. In this embodiment, the rest of the tensioner instrument, other than the arms, may be reusable or disposable, and may be integrally connected with the disposable arm 415 for use in a single procedure on a patient.

In a further embodiment, the present disclosure includes a system for the repair of soft tissue including at least one implant, at least one instrument for insertion of the implant, and a surgical procedure. A fixation member and/or other instrumentation discussed above may also be included in the system. The surgical procedure may include instructions or protocol for using the implant, fixation member, and/or the insertion instrument or any other instrument to repair soft tissue. The protocol may include aspects of any of the above-discussed embodiments, though other variations are also envisioned within the scope of the present disclosure.

In an associated embodiment, the present disclosure includes a method of providing instructions or information to practice any of the various methods of performing soft tissue repair described herein. For example, the method may include supplying a surgical protocol, or like document, to provide step-by-step instructions for performing any of the method embodiments of the present disclosure.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A tensioner comprising:
a body having a channel and a plurality of arms projecting outward from the body, each arm including a cleat having a slot adapted to receive a suture;
a base member positioned within the channel of the body;
an actuating mechanism having a first coupling member adapted to engage a second coupling member on the body to removeably couple the actuating mechanism to the body; and
a universal joint in the form of a portion of an outer surface of the base member having a convex surface and a portion of an inner surface of the body having a corresponding concave surface, the convex surface receivable within the concave surface to allow for relative movement between the base member and the body such that, when each suture is positioned within each cleat and the actuating mechanism is actuated, the tensioner applies uniform tension to each suture positioned in each cleat,
wherein the convex surface has a hemispherical shape.

2. The tensioner of claim 1, wherein the universal joint includes a a second portion of the outer surface of the base member forming a second convex surface and a second portion of the inner surface of the body forming a second concave surface, wherein the second concave surface receives the second convex surface.

3. The tensioner of claim 1, wherein the plurality of arms are laterally adjustable relative to the body.

4. The tensioner of claim 1, wherein the tensioner is movable between a rest condition in which the first coupling member of the actuating mechanism is engaged with the corresponding second coupling member of the body, such that the body is stationary relative to the base member, and an actuated condition in which the first coupling member and the second coupling member disengage to allow relative movement between the body and the base member.

5. The tensioner of claim 4, wherein the actuating mechanism is moveable between an initial position in which the tensioner is in the rest condition and a final position in which the tensioner is in the actuated condition.

6. The tensioner of claim 1, wherein each arm is pivotable in a plurality of directions relative to the body.

7. The tensioner of claim 1, wherein the first coupling member is a projection disposed on the actuating mechanism and the second coupling member is an opening on the body for receiving the projection.

8. The tensioner of claim 1, wherein the actuating mechanism is spring actuated.

9. The tensioner of claim 8, further comprising a tension gauge for indicating the amount of force applied to the spring.

10. The tensioner of claim 1, wherein the plurality of arms is four arms.

11. The tensioner of claim 1, further comprising a foot positioned on the base member.

12. The tensioner of claim 1, wherein the tensioner extends along a longitudinal axis, the tensioner being symmetrical on either side of the longitudinal axis.

13. The tensioner of claim 1, wherein the arms are positioned near a distal end of the body.

14. A tensioner comprising:
a body having a channel and a plurality of arms projecting outward from the body, each arm including a cleat having a slot adapted to receive a suture, the body having a hemispherically-shaped concave surface;

a base member positioned within the channel of the body and having a hemispherically-shaped convex surface; and an actuating mechanism having a first coupling member adapted to engage a second coupling member on the body to removeably couple the actuating mechanism to the body, wherein the hemispherically-shaped convex surface of the base member is received within the hemispherically-shaped concave surface of the body to allow relative movement of the body and the base member;

wherein the tensioner is movable between a rest condition in which the first coupling member of the actuating mechanism is engaged with the corresponding second coupling member of the body, such that the body is stationary relative to the base member, and an actuated condition in which the first coupling member and the second coupling member disengage to allow relative movement between the body and the base member.

15. The tensioner of claim 14, wherein the universal joint is adapted to allow for relative movement between the base member and the body such that, when each suture is positioned within each cleat and the tensioner is in the actuated condition, the tensioner applies uniform tension to each suture positioned in each cleat.

16. The tensioner of claim 15, wherein in the actuated condition, the arms are laterally adjustable relative to the body and pivotable in a plurality of directions.

17. The tensioner of claim 14, wherein the body includes a second concave surface and the base member includes a second convex surface and the second concave surface receives the second convex surface.

18. The tensioner of claim 14, further comprising a foot positioned on the base member.

19. The tensioner of claim 14, further comprising a tension gauge for indicating an amount of force applied to the actuating mechanism.

* * * * *